United States Patent
Burghardt et al.

(10) Patent No.: US 11,542,218 B2
(45) Date of Patent: *Jan. 3, 2023

(54) PROCESS FOR PREPARING METHACROLEIN FROM FORMALDEHYDE AND PROPIONALDEHYDE AND PREPARATION PLANT FOR THE PURPOSE

(71) Applicant: Röhm GmbH, Darmstadt (DE)

(72) Inventors: Rudolf Burghardt, Darmstadt (DE); Steffen Krill, Muehltal (DE); Florian Zschunke, Frankfurt (DE); Eduard Rundal, Frankfurt (DE); Torsten Panak, Stockstadt/Rhein (DE); Daniel Helmut König, Stuttgart (DE)

(73) Assignee: Röhm GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/753,232

(22) PCT Filed: Aug. 20, 2020

(86) PCT No.: PCT/EP2020/073355
§ 371 (c)(1),
(2) Date: Feb. 24, 2022

(87) PCT Pub. No.: WO2021/037671
PCT Pub. Date: Mar. 4, 2021

(65) Prior Publication Data
US 2022/0289656 A1 Sep. 15, 2022

(30) Foreign Application Priority Data
Aug. 30, 2019 (EP) ..................... 19194665

(51) Int. Cl.
*C07C 45/82* (2006.01)
*C07C 45/75* (2006.01)

(52) U.S. Cl.
CPC .............. *C07C 45/75* (2013.01); *C07C 45/82* (2013.01)

(58) Field of Classification Search
CPC ................ C07C 45/75; C07C 45/82
See application file for complete search history.

(56) References Cited

U.S. PATENT DOCUMENTS

| | | | |
|---|---|---|---|
| 4,496,770 A | 1/1985 | Duembgen et al. | |
| 9,580,374 B2 | 2/2017 | Krill et al. | |
| 9,611,204 B2 | 4/2017 | Burghardt et al. | |
| 9,816,703 B2 | 11/2017 | Krill et al. | |
| 9,890,105 B2 | 2/2018 | Krill et al. | |
| 9,994,507 B2 | 6/2018 | Burghardt et al. | |
| 10,125,077 B2 | 11/2018 | Krill et al. | |
| 2016/0068464 A1 | 3/2016 | Krill et al. | |
| 2016/0138804 A1 | 5/2016 | Krill et al. | |
| 2016/0159719 A1 | 6/2016 | Burghardt et al. | |
| 2016/0200660 A1 | 7/2016 | Krill et al. | |
| 2017/0275227 A1 | 9/2017 | Burghardt et al. | |
| 2017/0305830 A1 | 10/2017 | Krill et al. | |
| 2021/0363089 A1 | 11/2021 | Lygin et al. | |

FOREIGN PATENT DOCUMENTS

| | | |
|---|---|---|
| DE | 3213681 | 10/1983 |
| EP | 2829531 | 1/2015 |
| WO | 2015065610 | 7/2015 |
| WO | 2016/042000 | 3/2016 |
| WO | 2018/217961 | 11/2018 |
| WO | 2018/217963 | 11/2018 |
| WO | 2018/217964 | 11/2018 |

OTHER PUBLICATIONS

International Search Report dated Nov. 5, 2020 in PCT/EP2020/073355, with English translation, 5 pages.
Written Opinion dated Nov. 5, 2020 in PCT/EP2020/073355, with English translation, 11 pages.
U.S. Pat. No. 9,611,204, Apr. 4, 2017, 2016/0159719, Burghardt et al.
U.S. Appl. No. 177/269,648, filed Feb. 19, 2021, 2021/0363089, Lygin et al.
U.S. Pat. No. 9,816,703, Nov. 14, 2017, 2016/0138804, Krill et al.
U.S. Pat. No. 9,580,374, Feb. 28, 2017, 2016/0200660, Krill et al.
U.S. Pat. No. 9,994,507, Jun. 12, 2018, 2017/0275227, Burghardt et al.
U.S. Pat. No. 10,125,077, Nov. 13, 2018, 2017/0305830, Krill et al.
U.S. Pat. No. 9,890,105, Feb. 13, 2018, 2016/0068464, Krill et al.

*Primary Examiner* — Sikarl A Witherspoon
(74) *Attorney, Agent, or Firm* — Grüneberg and Myers PLLC

(57) ABSTRACT

A process and a preparation plant can prepare methacrolein from formaldehyde and propionaldehyde in the presence of a homogeneous catalyst mixture based at least on an acid and a base. For a good workup of the reaction mixture leaving the reactor, with a good energy balance and where the process has simplified apparatus implementation, the liquid reaction mixture under pressure is expanded in an expansion vessel and separated into a first expansion mixture in a gas phase and a second expansion mixture in a liquid phase. The first expansion mixture is condensed in a first condenser and the second expansion mixture is introduced into a first distillation column and separated therein, into a first distillation mixture in a gas phase at the top and a second distillation mixture in a liquid phase at the bottom. The first distillation mixture is condensed in the first condenser.

20 Claims, 5 Drawing Sheets

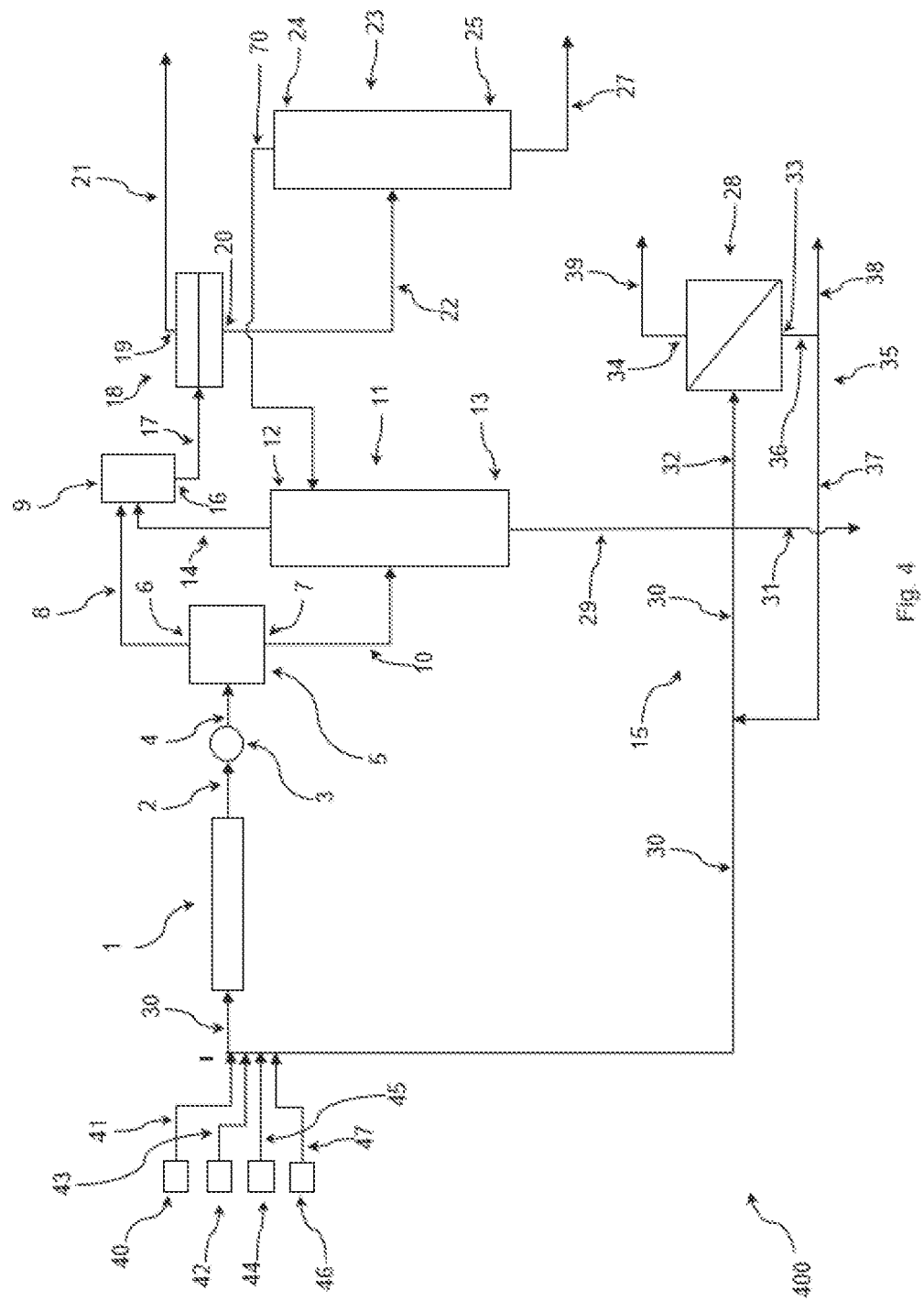

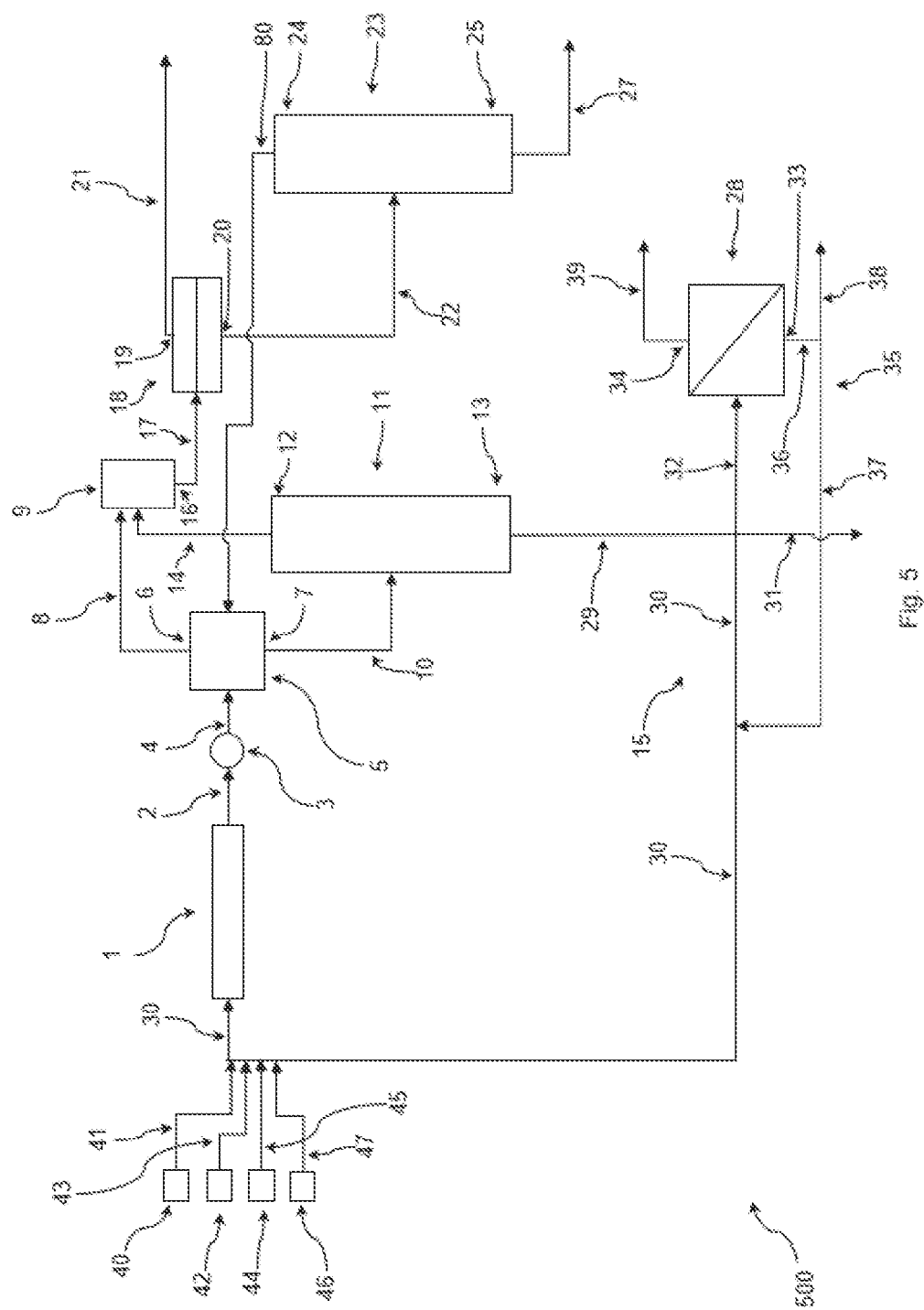

PROCESS FOR PREPARING METHACROLEIN FROM FORMALDEHYDE AND PROPIONALDEHYDE AND PREPARATION PLANT FOR THE PURPOSE

CROSS-REFERENCE TO RELATED APPLICATIONS

This application is the National Stage entry under § 371 of International Application No. PCT/EP2020/073355, filed on Aug. 20, 2020, and which claims the benefit of priority to European Application No. 19194665.6, filed on Aug. 30, 2019. The content of each of these applications is hereby incorporated by reference in its entirety.

BACKGROUND OF THE INVENTION

Field of the Invention

The present invention relates to a process and to a preparation plant for preparing methacrolein from formaldehyde and propionaldehyde in the presence of a homogeneous catalyst mixture based at least on an acid and a base.

Description of Related Art

The reaction is usually performed at relatively high temperatures in order to achieve higher reaction rates and hence a faster conversion of the formaldehyde and propionaldehyde reactants to methacrolein. If, however, the reaction mixture still containing the catalyst mixture remains at a relatively high temperature over a prolonged period of time, there is increasing formation of by-products and/or formation of dimethacrolein, which is undesirable. This is because the higher the demands on the purity of the final methacrolein product, the higher the complexity required for the removal of the by-products or of the dimethacrolein.

A route proposed in the prior art is to send the reaction mixture still containing the catalyst mixture as quickly as possible to a distillation column in which the catalyst mixture is removed. This route is taught, for example, by DE 3213681 A1. DE 3213681 A1 describes a process in which methacrolein is prepared in a tubular reactor under elevated pressure in the liquid phase from formaldehyde and propionaldehyde in the presence of a homogeneous catalyst mixture. The reaction mixture is expanded to standard pressure and routed into a first distillation column. A gaseous stream containing methacrolein and water is drawn off from the top of the first distillation column. Water and catalyst mixture collect in the bottom. The homogeneous catalyst mixture is thus removed in the first distillation column. In addition, DE 3213681 A1 proposes a reactor operation that gives good reaction results with only a small amount of catalyst mixture. In this way, less catalyst mixture is thus used from the outset.

For the handling of the aqueous phase removed, which contains the homogeneous catalyst mixture, DE 3213681 A1 proposes multiple variants. In a first variant, the bottoms are disposed of entirely. In a second variant, a portion of the bottoms is disposed of and the rest is returned to the reactor. In a third variant, the bottoms are sent to a second distillation column with which water is removed by distillation overhead. The concentration of the catalyst mixture in the bottoms from the second distillation column is thus correspondingly higher than in the bottoms from the first distillation column. The bottoms from the second distillation column are returned to the reactor. In a fourth variant, only a portion of the bottoms from the second distillation column is returned to the reactor and the rest is disposed of.

The first and second variants, compared to the third and fourth variants, are more energetically favourable and distinctly simpler in apparatus terms. However, more catalyst mixture is lost than in the third and fourth variant: in the first variant because the entire bottoms are disposed of, and in the second variant because it is not possible to return an arbitrarily large amount of water to the reactor and therefore the amount of recyclable catalyst mixture is smaller. However, when the content of catalyst mixture in the bottoms from the first distillation column is so high that the bottoms cannot be released as wastewater into a communal water treatment plant, the second, third and fourth variants are suitable for reducing the amount of problematic wastewater. In the second variant this is accomplished by recycling a portion of the bottoms from the first distillation column into the reactor, in the third variant in that the distillative removal of water enables returning of the entire bottoms from the second distillation column to the reactor and consequently no occurrence of problematic wastewater, and in the fourth variant in that the distillative removal of water and the partial recycling of the bottoms from the second distillation column into the reactor further reduces the amount of problematic wastewater compared to the second variant.

The top stream from the first distillation column is condensed in a condenser. The condensate is separated in a liquid-liquid phase separator into a liquid organic phase containing mainly methacrolein and a liquid aqueous phase. The organic phase is collected in a collecting vessel as product. The aqueous phase is routed back into the first distillation column.

WO 2016/042000 A1 also proposes a process in which the reaction mixture still containing the catalyst mixture is sent very quickly to a distillation column in which the catalyst mixture is removed. Methacrolein is prepared in a tubular reactor under elevated pressure in the liquid phase from formaldehyde and propionaldehyde in the presence of a homogeneous catalyst mixture. The reaction mixture is expanded and routed into a first distillation column. A gaseous top stream containing methacrolein and water is drawn off from the top of the first distillation column. Water and catalyst mixture accumulate in the bottoms from the first distillation column. The homogeneous catalyst mixture is thus removed in the first distillation column.

With regard to the handling of the phase removed, containing the homogeneous catalyst mixture, WO 2016/042000 A1 proposes returning the bottoms from the first distillation column, apart from a portion returned to the first distillation column, at least partly into the reactor. The portion not returned to the reactor is sent to a workup or disposal. The workup can be effected in a second distillation column or in a membrane separation stage.

The top stream from the first distillation column is condensed. The condensate is routed into a liquid-liquid phase separator in which a liquid organic phase and a liquid aqueous phase are separated from one another. The organic phase contains methacrolein in such a high concentration that it is removed as product stream. The aqueous phase is wholly or partly returned to the first distillation column.

EP 2829531 A1 is a further publication that proposes a process in which the reaction mixture still containing the catalyst mixture is sent very quickly to a distillation column in which the catalyst mixture is removed. Methacrolein is prepared in a tubular reactor under elevated pressure in the liquid phase from formaldehyde and propionaldehyde in the presence of a homogeneous catalyst mixture. The reaction mixture is expanded and routed into a distillation column. A gaseous top stream containing methacrolein and water is drawn off from the top of the distillation column. Water and catalyst mixture accumulate in the bottom of the distillation column. The homogeneous catalyst mixture is thus removed in the distillation column.

For the further handling of the aqueous phase removed, containing the homogeneous catalyst mixture, EP 2829531 A1 proposes returning a portion of the bottom stream to the reactor and sending the other portion to a workup by a membrane separation stage. The retentate from the membrane separation stage in which the catalyst mixture is enriched is at least partly recycled into the reactor. The portion of the retentate that has not been recycled is sent to disposal. The permeate as the less contaminated aqueous phase is sent separately to a disposal.

Rather than one membrane separation stage, it is also possible to provide two membrane separation stages.

The top stream from the distillation column is condensed. The condensate is routed into a liquid-liquid phase separator in which a liquid organic phase and a liquid aqueous phase are separated from one another. The organic phase contains methacrolein in such a high concentration that it is removed as product stream. The aqueous phase is returned to the distillation column.

Another route proposed in the prior art is to significantly cool the reaction mixture in order to distinctly reduce side reactions and/or the formation of dimethacrolein. This gains time for the further workup of the reaction mixture. This route is proposed as an alternative in EP 2829531 A1.

The reaction mixture is cooled, which is associated with corresponding expansion, and routed into a liquid-liquid phase separator upstream of the distillation column. In the liquid-liquid phase separator, a liquid organic phase containing a high proportion or methacrolein is separated from a liquid aqueous phase containing the homogeneous catalyst mixture. This separating operation takes a while, and this time is available by virtue of the significant cooling of the reaction mixture.

The removal of the aqueous phase not only separates a large portion of the catalyst mixture from the organic phase. Since only the organic phase is routed into the distillation column, much less water is also introduced into the distillation column. This means that, firstly, a mixture of greater purity from the outset is introduced into the distillation column, which leads to an even cleaner top stream from the distillation column. Secondly, a smaller amount is also introduced into the first distillation column, and so a correspondingly smaller amount has to be heated therein, and the distillation column can also have a smaller design.

With regard to the bottoms from the distillation column, EP 2829531 A1 in this case proposes returning it to the liquid-liquid phase separator in a first variant, routing it into the membrane separation stage in a second variant, into which at least a portion of the aqueous phase from the liquid-liquid phase separator is also routed, returning it to the reactor in a third variant, as is also possible for a portion of the aqueous phase from the liquid-liquid phase separator, or sending it to disposal in a fourth variant.

WO 2018/217961 A1 is a further publication that proposes the route of significantly cooling the reaction mixture in order to distinctly reduce side reactions and/or the formation of dimethacrolein. It discloses a process for preparing methacrolein from formaldehyde and propionaldehyde in the presence of a homogeneous catalyst mixture, in which the reaction is conducted at temperatures of more than 100° C., for example at temperatures of 150-220° C., and elevated pressure in the liquid phase. The reaction mixture containing the homogeneous catalyst mixture is significantly cooled, namely to less than 15° C., preferably to less than 5° C. The cooling also accomplishes a corresponding reduction in pressure. The cooled reaction mixture is routed into a first liquid-liquid phase separator in which a liquid organic phase containing a high proportion of methacrolein and a liquid aqueous phase including homogeneous catalyst mixture are separated from one another. The aqueous phase is routed into a first distillation column, and the organic phase into a second distillation column. By virtue or the prior separation of aqueous and organic phases, not only was a large portion of the catalyst mixture separated from the organic phase. The first and second distillation column is also supplied with a mixture of greater purity from the outset, which leads to even purer top and bottom streams from the first and second distillation columns.

An aqueous side stream is additionally removed from the first distillation column in order to reduce the water content in the bottom of the first distillation column, which increases the concentration of the catalyst mixture in the bottom of the first distillation column. Since it is not possible to return an arbitrarily large amount of water to the reactor, the amount of the catalyst mixture returnable to the reactor is thus increased and the amount of problematic wastewater that has to be disposed of is reduced.

A portion of the bottoms from the first distillation column is returned to the reactor, a further portion is discharged, and the remaining portion is returned to the first distillation column.

The top stream from the first distillation column is condensed and routed into a second liquid-liquid phase separator in which a liquid organic phase and a liquid aqueous phase are separated from one another. In order to wash out methanol present in the top stream from the first distillation column, the second liquid-liquid phase separator is supplied with additional water. The liquid aqueous phase is discharged. The liquid organic phase from the second liquid-liquid phase separator is likewise routed into the second distillation column. The top stream from the second distillation column is condensed and routed into the first liquid-liquid phase separator. The bottoms from the second distillation column containing predominantly methacrolein, apart from a portion routed back into the second distillation column, are routed into a third distillation column. Unwanted organic components are removed via the bottoms from the third distillation column. The top stream from the third distillation column is condensed and contains methacrolein in high purity.

WO 2018/217963 A1 discloses a process for preparing methacrolein from formaldehyde and propionaldehyde in the presence of a homogeneous catalyst mixture, which differs from the process known from WO 2018/217961 A1 particularly in that the top stream from the first distillation column, after being condensed, is not routed into a second liquid-liquid phase separator but removed as a second product stream.

WO 2018/217964 A1 discloses a process for preparing methacrolein from formaldehyde and propionaldehyde in the presence of a homogeneous catalyst mixture, which differs from the process known from WO 2018/217963 A1 particularly in that the top stream from the second distillation column is not recycled partly into the liquid-liquid phase separator connected upstream of the first and second distillation columns, but discharged completely as the first product stream, and bottoms from the second distillation column are not routed into a third distillation column, but are a waste stream and discharged.

WO 2015/065610 A1 also proposes the route of significantly cooling the reaction mixture in order to distinctly reduce side reactions and/or the formation of dimethacrolein. It discloses a process for preparing methacrolein from formaldehyde and propionaldehyde in the presence of a homogeneous catalyst mixture, which differs from the process known from WO 2018/217963 A1 particularly in that
- the top stream from the first distillation column is not removed as the second product stream but, after being condensed, routed partly into the first distillation column and into the liquid-liquid phase separator which is connected upstream of the first and the second distillation columns and takes the form of a decanter,
- bottoms from the second distillation column are not routed into a third distillation column, but are removed directly as a product stream, and
- a portion of the condensed top stream from the second distillation column is returned to the second distillation column.

The process can be developed in such a way that a portion of the condensed top stream from the second distillation column is routed into a separate decanter and a liquid organic phase removed in this decanter is routed into the second distillation column and/or is added to the bottom stream from the second distillation column. It can also be developed in such a way that a portion of the condensed top stream from the first distillation column is routed into a further separate decanter and a liquid organic phase removed in this decanter is routed into the second distillation column and a liquid aqueous phase removed in this decanter is routed into the first distillation column.

SUMMARY OF THE INVENTION

It is an object of the present invention to provide a process for preparing methacrolein from formaldehyde and propionaldehyde in the presence of a catalyst based at least on an acid and a base, with which good workup of the reaction mixture leaving the reactor can be performed with a good energy balance and which is implementable with maximum simplicity in apparatus terms. It is a further object of the invention to provide a corresponding preparation plant.

The process object is achieved in accordance with the invention by a process having the features as described below. The reaction mixture leaving the reactor is liquid and is under pressure. The expansion of this liquid reaction mixture causes a fraction of the reaction mixture to go into the gas phase, which gives rise to the first expansion mixture, i.e. the fraction of the reaction mixture that has been converted to the gas phase by the expansion, and the second expansion mixture, i.e. the fraction of the reaction mixture that has remained in the liquid phase. The methacrolein content in the first expansion mixture is higher than in the second expansion mixture. Consequently, the relief of the pressure is already a step for obtaining a mixture having an elevated methacrolein content. The first expansion mixture and the second expansion mixture are separated from one another in the expansion vessel.

BRIEF DESCRIPTION OF THE DRAWINGS

FIG. 4 shows a fourth embodiment of the invention illustrated by a schematic flow diagram.

FIG. 5 shows a fifth embodiment of the invention illustrated by a schematic flow diagram.

DETAILED DESCRIPTION OF THE INVENTION

Figure 1:
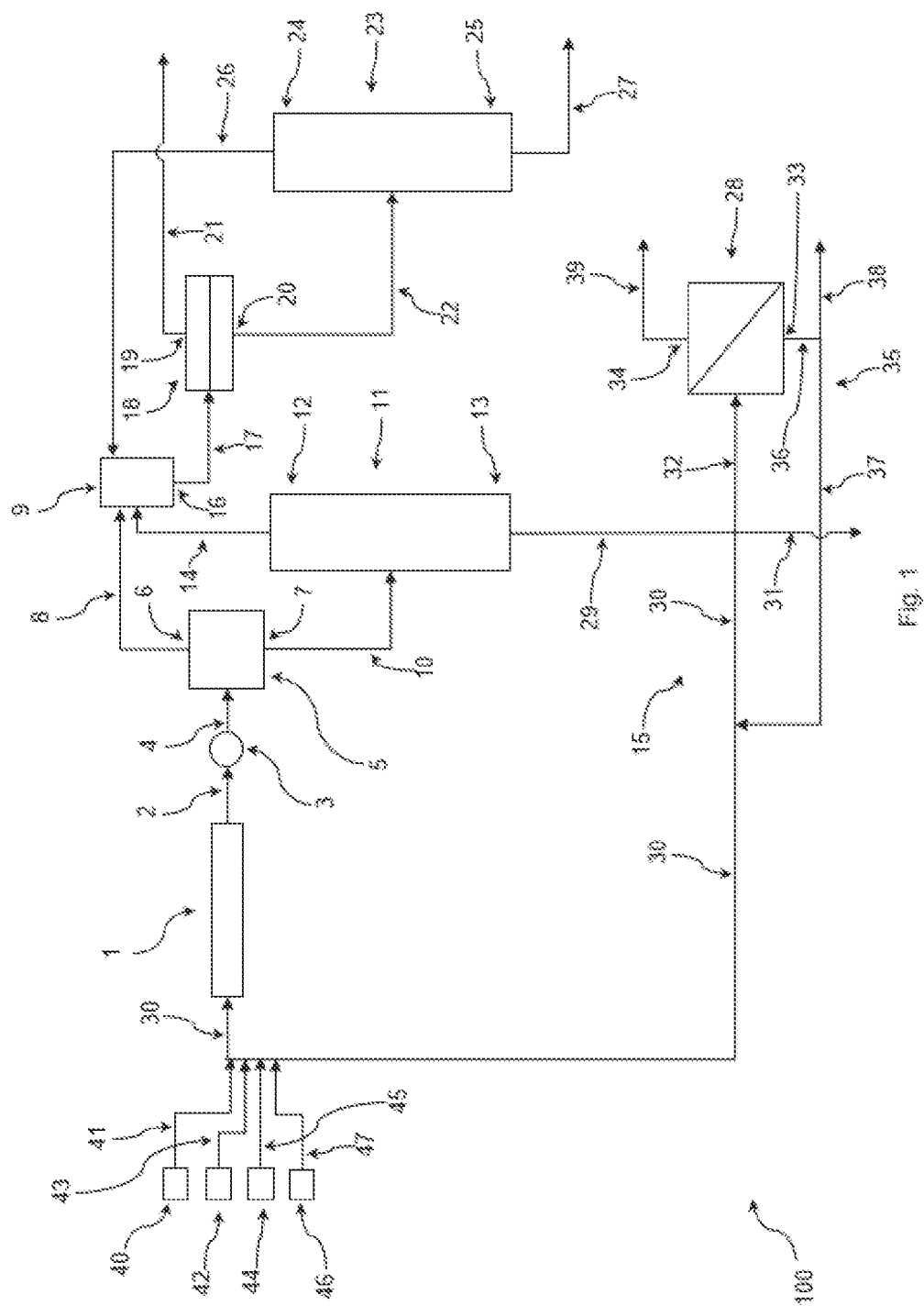
FIG. 1 shows a first embodiment of the invention illustrated by a schematic flow diagram.

The relief of the pressure is accompanied by cooling. There is thus no need for any additional energy expenditure or apparatus complexity for this cooling. In addition, the amount of energy corresponding to the reduction of pressure remains in the system in spite of the cooling associated with the reduction in pressure.

Only the second expansion mixture has to be routed into the first distillation column and heated for the distillation operation. The first expansion mixture is routed straight into the first condenser and condensed therein together with the first distillation mixture coming from the top of the first distillation column.

Preferably, the reaction mixture, immediately prior to the execution of step S3, has a temperature selected from the range from 100 to 210° C. preferably a temperature selected from the range from 130 to 180° C., and is at a pressure selected from the range from 15 to 100 bar (absolute), preferably with a pressure selected from the range from 22 to 50 bar (absolute), wherein the pressure is selected such that the reaction mixture in the reactor (1) remains liquid at the selected temperature. At a temperature in the range from 100 to 210° C. and a pressure in the range from 15 to 100 bar (absolute), it is possible to generate a good proportion of the first expansion mixture by virtue of the expansion. At a temperature in the range from 130 to 180° C. and a pressure in the range from 22 to 50 bar (absolute), it is possible to generate a good proportion of the first expansion mixture by virtue of the expansion, this proportion being in a good relationship to the compression energy and thermal energy applied.

Advantageously, condensate from the first condenser may be routed into a first phase separator and separated in the first phase separator into a first separation mixture and a second separation mixture, wherein the first separation mixture is in the form of an organic phase comprising methacrolein, and the second separation mixture is in the form of an aqueous phase. In this way, in a simple and effective manner, the aqueous phase, and hence a large amount of water, is separated from the organic phase which can contain a high proportion of methacrolein.

Preferably, the second separation mixture may be routed into a second distillation column and separated therein at least into a third distillation mixture and a fourth distillation mixture, wherein the third distillation mixture is in the form of a gas phase at the top of the second distillation column, and the fourth distillation mixture is present at the bottom of the second distillation column and comprises water. In this way, it is possible to draw off a good portion of methacrolein present in the second separation mixture overhead. Since the catalyst mixture also collects in the bottom of the first distillation column and the amount of catalyst mixture present in the second separation mixture is correspondingly small, it is possible in the second distillation column to obtain a bottoms liquid contaminated only to a minor degree with problematic substances, which is advantageous with regard to its disposal.

More preferably, third distillation mixture may be removed from the top of the second distillation column and introduced into the first condenser. As a result, no dedicated condenser and phase separator is required for the third distillation mixture, and the apparatus complexity is reduced in that respect. In the first condenser, the third distillation mixture is converted to its condensate, which is routed into the first phase separator.

In an advantageous embodiment of the invention, the third distillation mixture may be introduced into and condensed in a second condenser, and condensate may be removed from the second condenser and introduced into the first phase separator. The second condenser can condense the third distillation mixture independently of the first condenser. In addition, the second condenser can be utilized for at least partial recycling of the third distillation mixture into the second distillation column.

Particularly advantageously, third distillation mixture may be introduced into and condensed in a second condenser, and condensate may be removed from the second condenser and introduced into a second phase separator and may be separated in the second phase separator into a third separation mixture and a fourth separation mixture, wherein the third separation mixture is in the form of an organic phase comprising methacrolein, and the fourth separation mixture is in the form of an aqueous phase. By virtue of the separation conducted by means of the second phase separator, it is possible to utilize the third separation mixture as a product stream with a good degree of methacrolein workup separate from the first separation mixture, or to combine it with the first separation mixture to give a common product stream with a good degree of methacrolein workup. In other words, the third separation mixture need not necessarily be introduced into the first phase separator. Moreover, it is especially possible with the second condenser and the second phase separator to return a fraction of the third distillation mixture to the second distillation column, namely the fourth separation mixture, and hence conduct a particularly good separation in the second distillation column, especially a particularly good separation of methacrolein on the one hand and water on the other.

More preferably, the third distillation mixture is introduced into the first distillation column. In this way, the third distillation mixture is sent to the workup conducted by means of the first distillation column and the first phase separator.

Advantageously, third distillation mixture is introduced into the expansion vessel. In this way, the third distillation mixture is sent via the route via the expansion vessel to the workup conducted by means of the first distillation column and the first phase separator.

In a favourable variant, second separation mixture may be introduced into the first distillation column. This recycling of second separation mixture into the first distillation column can improve the purity of the first distillation mixture, i.e. the proportion of the substances in the first distillation mixture that are to be removed overhead in the first distillation column can be increased by the recycling mentioned. Moreover, the second separation mixture recycled can be used to counteract the entrainment of drops and/or droplets overhead in the first distillation column therefrom.

The apparatus object is achieved in accordance with the invention by a preparation plant having the features as described. The reaction mixture leaving the reactor is liquid and is under pressure. If it is expanded, a fraction of the reaction mixture goes into the gas phase, which gives rise to the first expansion mixture, and a fraction of the reaction mixture remains in the liquid phase, which gives rise to the second expansion mixture. The methacrolein content of the first expansion mixture is higher than the methacrolein content of the second expansion mixture. The relief of the pressure is consequently a step for obtaining a mixture having an elevated methacrolein content. The expansion vessel can separate first and second expansion mixture from one another, and hence each can be sent separately to further workup steps.

The expansion is accompanied by cooling. This cooling thus does not require any additional apparatus complexity or energy expenditure. In addition, the amount of energy corresponding to the reduction in pressure remains in the system in spite of the cooling associated with the reduction in pressure.

Only the second expansion mixture has to be routed into the first distillation column and heated for the distillation operation. The first expansion mixture may be routed straight into the first condenser and condensed therein with the first distillation mixture coming from the top of the first distillation column. For this purpose, the first distillation column is fluidically connected to the second outlet of the expansion vessel, and the first condenser is fluidically connected to the first outlet of the expansion vessel and the top of the first distillation column.

Preferably, the preparation plant may have a first phase separator which is fluidically connected to the first condenser and with which a first separation mixture of organic phase present in the condensate supplied by the first condenser may be separated from a second separation mixture of aqueous phase present in the condensate supplied by the first condenser, wherein the first phase separator may have a first outlet for removing first separation mixture and a second outlet for removing second separation mixture. With this setup, in a simple and effective manner, the aqueous phase, and hence a large amount of water, may be separated from the organic phase which can contain a high proportion of methacrolein.

Particularly advantageously, the preparation plant may have a second distillation column which has a top and a bottom and with which second separation mixture may be separated at least into a methacrolein-containing third distillation mixture in the form of a gas phase and a water-containing fourth distillation mixture in the form of a liquid phase, and a phase separator removal conduit arrangement which connects the second distillation column to the second outlet of the first phase separator, and which can route second separation mixture from the second outlet of the first phase separator into the second distillation column. With the second distillation column, it is still possible to remove a good portion of the methacrolein present in the second separation mixture—present in the third distillation mixture drawn off overhead. Since the amount of catalyst mixture present in the second separation mixture is correspondingly small, a residue collecting in the bottom of the second distillation column and contaminated only to a minor degree with problematic substances may be obtained, which is advantageous with regard to its disposal.

More preferably, a distillation column removal conduit arrangement may fluidically connect the top of the second distillation column to the first condenser, and third distillation mixture may be routed through the distillation column removal conduit arrangement from the top of the second distillation column into the first condenser. By virtue of this setup, it is possible to condense third distillation mixture in the first condenser. Consequently, no separate condenser is required to condense the third distillation mixture, and the apparatus complexity is reduced in that respect. In the first condenser, the third distillation mixture is converted to its condensate, which may be routed into the first phase separator.

Advantageously, the preparation plant may have a second condenser and a distillation column removal conduit arrangement that fluidically connects the top of the second distillation column to the second condenser, wherein third distillation mixture may be routed through the distillation column removal conduit arrangement from the top of the second distillation column into the second condenser and may be condensed in the second condenser, and wherein the second condenser may be fluidically connected to the first phase separator, by means of which condensate from the second condenser can be routed from the second condenser further into the first phase separator. The second condenser can condense the third distillation mixture independently of the first condenser. In addition, the second condenser can be utilized for at least partial recycling of the third distillation mixture into the second distillation column.

Preferably, the preparation plant may have a second condenser, a distillation column removal conduit arrangement that fluidically connects the top of the second distillation column to the second condenser, wherein third distillation mixture may be routed through the distillation column removal conduit arrangement from the top of the second distillation column into the second condenser and condensed in the second condenser, and a second phase separator fluidically connected to the second condenser, by means of which condensate from the second condenser may be routed from the second condenser further into the second phase separator, with which a third separation mixture of organic phase present in the condensate supplied by the second condenser may be separated from a fourth separation mixture of aqueous phase present in the condensate supplied by the second condenser, wherein the second phase separator may have a first outlet for removal of third separation mixture and a second outlet for removal of fourth separation mixture. By virtue of the separation performable by means of the second phase separator, it is possible to utilize the third separation mixture as a product stream with a good degree of methacrolein workup separate from the first separation mixture, or to combine it with the third separation mixture to give a common product stream with a good degree of methacrolein workup. In other words, the third separation mixture need not necessarily be introduced into the first phase separator. Moreover, it is especially possible with the second condenser and the second phase separator to return a fraction of the third distillation mixture to the second distillation column, namely the fourth separation mixture, and hence conduct a particularly good separation in the second distillation column, especially a good separation of methacrolein on the one hand and water on the other.

Particularly advantageously, a distillation column removal conduit arrangement may fluidically connect the top of the second distillation column to the first distillation column, and third distillation mixture may be routed through the distillation column removal conduit arrangement from the top or the second distillation column into the first distillation column. As a result, third distillation mixture may be sent to the workup conducted by means of the first distillation column and the first phase separator.

Preferably, a distillation column removal conduit arrangement may fluidically connect the top of the second distillation column to the expansion vessel, and third distillation mixture may be routed through the distillation column removal conduit arrangement from the top of the second distillation column into the expansion vessel. With this setup, the third distillation mixture may be sent via the route via the expansion vessel to the workup conducted by means of the first distillation column and the first phase separator.

In a favourable embodiment, a phase separator removal conduit arrangement that connects the first distillation column to the second outlet of the first phase separator may be provided, by means of which second separation mixture can be routed from the second outlet of the first phase separator into the first distillation column. As a result, recycling of second separation mixture into the first distillation column is possible, which can improve the purity of the first distillation mixture, i.e. the proportion of the substances in the first distillation mixture that are to be removed overhead in the first distillation column can be increased by the recycling mentioned. Moreover, the second separation mixture recycled can be used to counteract the entrainment of drops and/or droplets overhead in the first distillation column therefrom.

More preferably, the preparation plant can be used for preparation of methacrolein, especially for preparation of methacrolein from formaldehyde and propionaldehyde in the presence of a homogeneous catalyst mixture based at least on an acid and a base.

Figure 2:
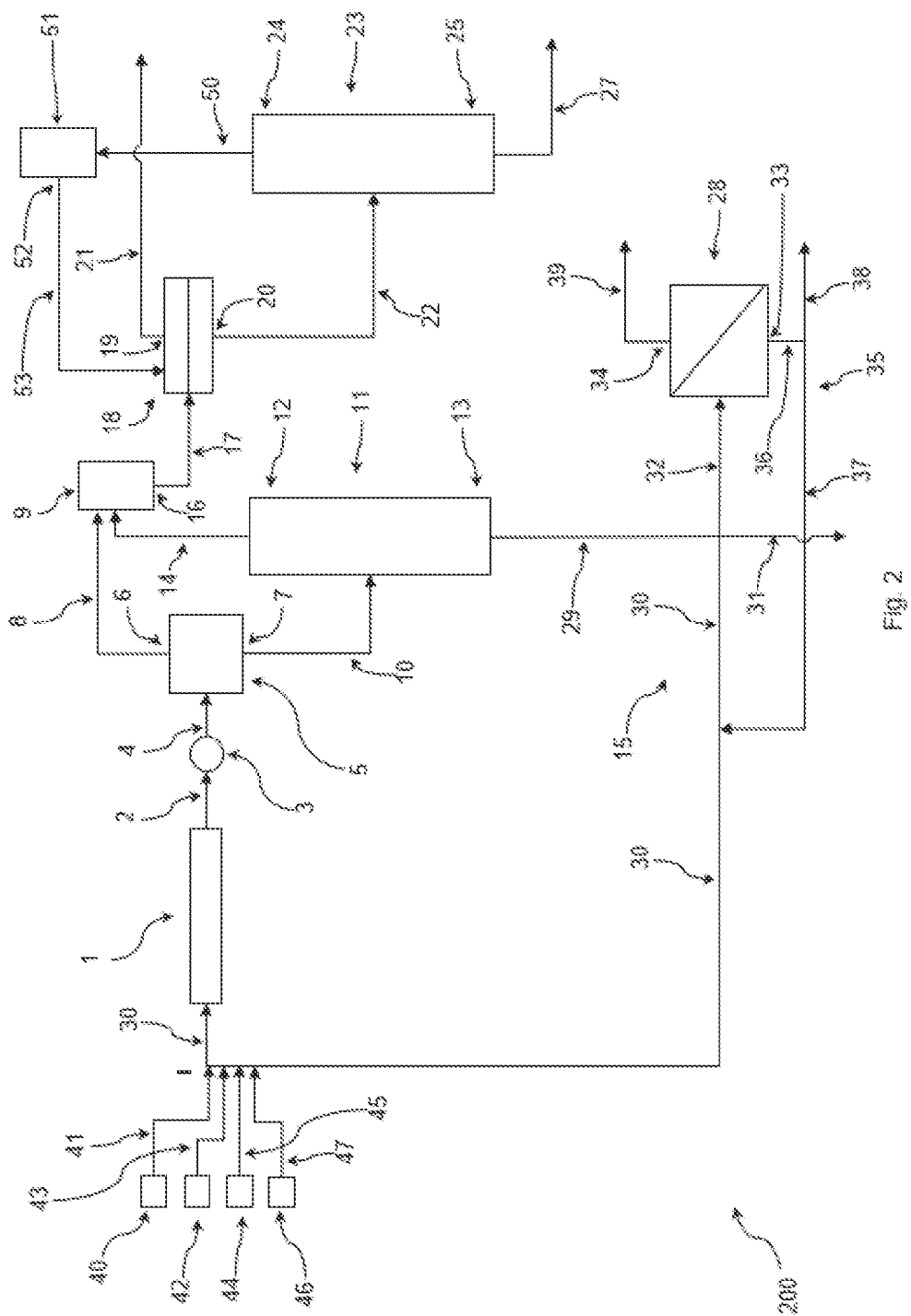
FIG. 2 shows a second embodiment of the invention illustrated by a schematic flow diagram.

The figures show some possible embodiments of the present invention. In the drawings:

FIG. 1 shows a first embodiment of the invention illustrated by a schematic flow diagram, FIG. 2 shows a second embodiment of the invention illustrated by a schematic flow diagram.

Figure 3:
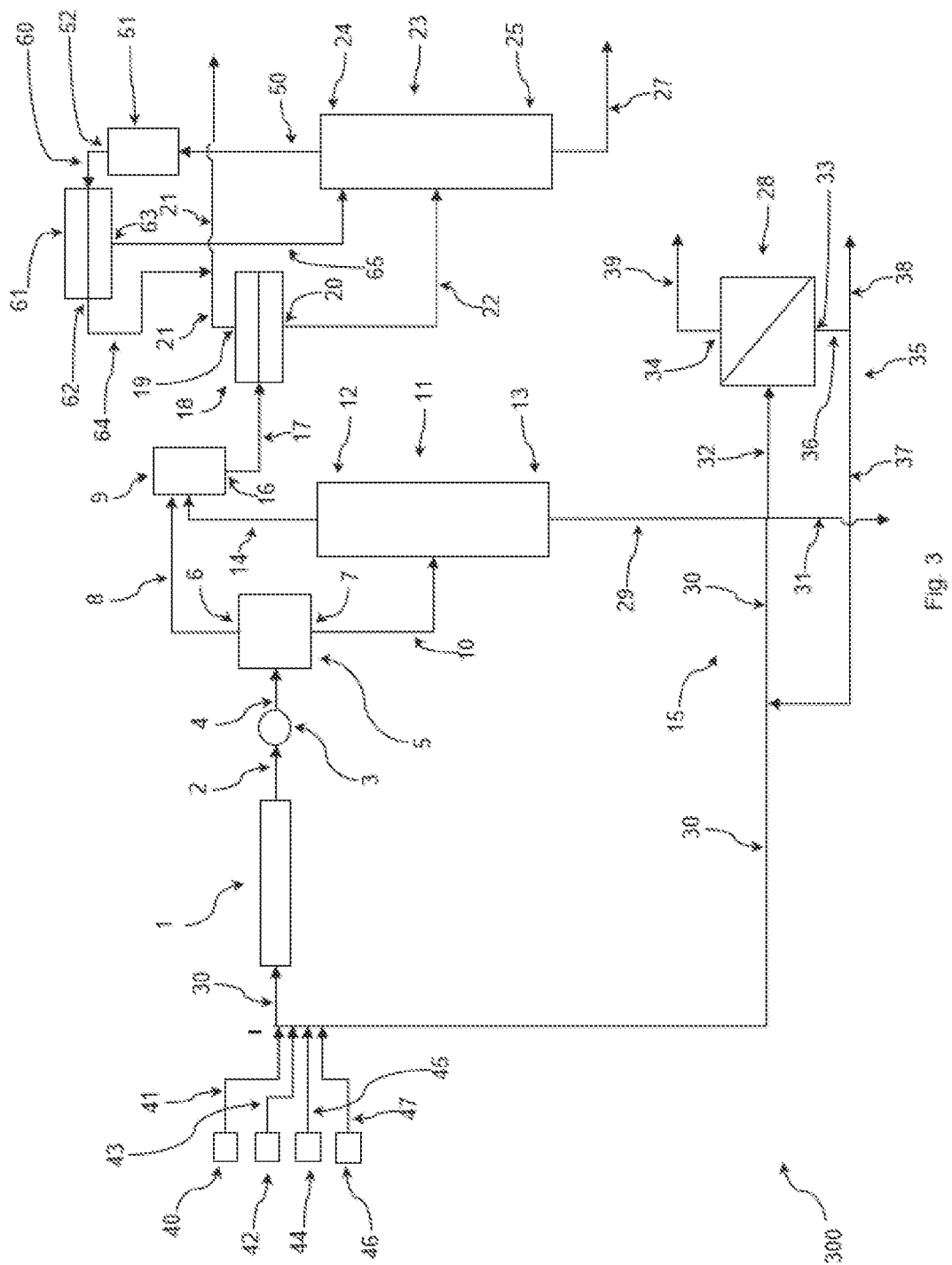
FIG. 3 shows a third embodiment of the invention illustrated by a schematic flow diagram.

FIG. 3 shows a third embodiment of the invention illustrated by a schematic flow diagram.

FIG. 4 shows a fourth embodiment of the invention Illustrated by a schematic flow diagram and FIG. 5 shows a fifth embodiment of the invention Illustrated by a schematic flow diagram.

In the schematic flow diagrams in FIGS. 1 to 5, the arrows indicate the flow direction of the respective medium in the course of performance of the process in question. If the arrows were omitted, FIGS. 1 to 5 would be schematic diagrams of the preparation plants of the first to fifth embodiments of the invention.

Reference is made to FIG. 1. The preparation plant 100 of the first embodiment of the invention Illustrated therein has a reactor 1 in which a reaction can be conducted in the liquid phase under elevated pressure, in which methacrolein is formed from formaldehyde and propionaldehyde in the presence of water and in the presence of a homogeneous catalyst based at least on an acid and a base. A reactor removal conduit arrangement 2 fluidically connect the reactor 1 to an expansion valve 3, by means of which reaction mixture can be routed from the reactor 1 through the reactor removal conduit arrangement 2 to the expansion valve 3. The expansion valve 3 can expand reaction mixture under elevated pressure coming from the reactor 1 to a lower pressure, and the expansion valve 3 can simultaneously regulate the pressure in the reactor 1. The expansion valve 3 could also be described as a pressure-retaining and expansion valve.

The expansion valve 3 is fluidically connected to an expansion vessel 5 or the preparation plant 100, specifically via an expansion valve removal conduit arrangement 4. The expansion vessel 5 can be used to separate a first expansion mixture which is the fraction of the reaction mixture that goes into the gas phase as a result of an expansion of reaction mixture, and a second expansion mixture which is the fraction of the reaction mixture that remains in the liquid phase after the expansion of the reaction mixture. The expansion vessel 5 may also be referred to as an expansion drum, although it need not have the shape of a drum, or as a flashbox.

The expansion vessel 5 has a first outlet 6 for removal of first expansion mixture and a second outlet 7 for removal of second expansion mixture.

The preparation plant 100 also has a first condenser 9. The first outlet 8 of the expansion vessel 5 is fluidically connected to the first condenser 9 via a first expansion vessel removal conduit arrangement 8, by means of which first expansion mixture can be routed from the expansion vessel 5 into the first condenser 9. The first condenser 9 can be used to condense first expansion mixture.

The preparation plant 100 also has a first distillation column 11 having a top 12 and a bottom 13. The second outlet 7 of the expansion vessel 5 is fluidically connected to the first distillation column 11 via a second expansion vessel removal conduit arrangement 10. It being possible to route second expansion mixture through the second expansion vessel removal conduit arrangement 10 from the expansion vessel 5 into the first distillation column 11. The first distillation column 11 can be used to separate second expansion mixture into a first distillation mixture in the form of a gas phase, containing methacrolein, and a second distillation mixture in the form of a liquid phase, containing water and catalyst.

By means of a first distillation column removal conduit arrangement 14, the top 12 of the first distillation column 11 is fluidically connected to the first condenser 9. The first distillation column removal conduit arrangement 14 can route first distillation mixture from the top 12 of the first distillation column 11 into the first condenser 9. The first distillation mixture supplied can be condensed in the first condenser 9.

The first expansion vessel removal conduit arrangement 8 and the first distillation column removal conduit arrangement 14 are each connected to a dedicated inlet of the first condenser 9.

The bottom 13 of the first distillation column 11 is fluidically connected to the reactor 1 by a second distillation column removal conduit arrangement 15. The second distillation column removal conduit arrangement 15 can route second distillation mixture from the first distillation column 11 into the reactor 1.

The preparation plant 100 also has a first phase separator 18. The first phase separator 18 is fluidically connected via a condenser removal conduit arrangement 17 to a condensate outlet 16 of the first condenser 9. The condenser removal conduit arrangement 17 can route condensate from the first condenser 9 from the first condenser 9 into the first phase separator 18. The first phase separator 18 can separate a first separation mixture of organic phase present in the condensate from the first condenser 9 from a second separation mixture of aqueous phase present in the condensate from the first condenser 9. The first phase separator 18 has a first outlet 19 for removal of first separation mixture and a second outlet 20 for removal of second separation mixture. By means of a first phase separator removal conduit arrangement 21 fluidically connected to the first outlet 19 of the first phase separator 18, first separation mixture can be removed from the first phase separator 18. By means of a second phase separator removal conduit arrangement 22 fluidically connected to the second outlet 20, second separation mixture can be removed from the first phase separator 18.

The preparation plant 100 also has a second distillation column 23 having a top 24 and a bottom 25. The second phase separator removal conduit arrangement 22 fluidically connects the second outlet 20 of the first phase separator 18 to the second distillation column 23. The second phase separator removal conduit arrangement 22 can route second separation mixture from the second outlet of the first phase separator 18 into the second distillation column 23. The second distillation column 23 can separate second separation mixture at least into a methacrolein-containing third distillation mixture in the form of a gas phase and a water-containing fourth distillation mixture in the form of a liquid phase.

A third distillation column removal conduit arrangement 26 is fluidically connected to the top 24 of the second distillation column 23. The third distillation column removal conduit arrangement 26 fluidically connects the top 24 of the second distillation column 23 to the first condenser 9, it being possible to route third distillation mixture through the third distillation column removal conduit arrangement 26 from the top 24 of the second distillation column 23 into the first condenser 9.

The third distillation column removal conduit arrangement 26 is connected to a dedicated inlet of the first condenser 9.

By means of a fourth distillation column removal conduit arrangement 27 fluidically connected to the bottom 25 of the second distillation column 23, fourth distillation mixture can be removed from the second distillation column 23.

The preparation plant 100 has a membrane plant 28 fluidically connected to the bottom 13 of the first distillation column 11. The membrane plant 28 is fluidically connected to the bottom 13 of the first distillation column 11 by the second distillation column removal conduit arrangement 15, it being possible to route second distillation mixture through the second distillation column removal conduit arrangement 15 from the bottom 13 of the first distillation column 11 into the membrane plant 28.

The second distillation column removal conduit arrangement 15 can also remove second separation mixture from the preparation plant 100.

The second distillation column removal conduit arrangement 15 of the embodiment shown in FIG. 1 has a first section 29, a second section 30, a third section 31 and a fourth section 32. The first section 29 is fluidically connected firstly to the bottom 13 of the first distillation column 11, and secondly to the second section 30, the third section 31 and the fourth section 32.

The second section 30 is fluidically connected to the reactor 1, by means of which second distillation mixture can be routed from the bottom 13 of the first distillation column 11 through the first and second sections 29, 30 of the second distillation column removal conduit arrangement 15 from the bottom 13 of the first distillation column 11 into the reactor 1.

By means of the first and third sections 29, 31 of the second distillation column removal conduit arrangement 15, it is possible to remove second distillation mixture from the preparation plant 100.

The fourth section 32 is fluidically connected to the membrane plant 28, by means of which second distillation mixture can be routed through the first and fourth sections 29, 32 of the second distillation column removal conduit arrangement 15 from the bottom 13 of the first distillation column 11 into the membrane plant 28.

The membrane plant 28 can retain at least a portion of the catalyst present in the second distillation mixture fed to the membrane plant 28. The membrane plant 28 has a first outlet 33 for removal of retentate mixture containing the retained catalyst, and a second outlet 34 for removal of permeate mixture. The first outlet 33 is fluidically connected to a first membrane plant removal conduit arrangement 35, by means of which retentate mixture can be removed from the membrane plant 28 via the first outlet 33 from the membrane plant 28.

In the working example shown in FIG. 1, the first membrane plant removal conduit arrangement 35 has a first section 38, a second section 37 and a third section 38. The first section 38 is fluidically connected firstly to the first outlet 33 of the membrane plant 28 and secondly to the second section 37 and the third section 38 of the first membrane plant removal conduit arrangement 35. The second section 37 of the first membrane plant removal conduit arrangement 35 is fluidically connected to the second section 30 of the second distillation column removal conduit arrangement 15, by means of which retentate mixture may be routed from the membrane plant 28 via the first outlet 33 thereof and the first and second sections 38, 37 of the first membrane plant removal conduit arrangement 35 into the second section 30 of the second distillation column removal conduit arrangement 15, and further through the latter into the reactor 1.

The first and third sections 38, 38 of the first membrane plant removal conduit arrangement 35 can remove retentate mixture from the preparation plant 100.

A second membrane plant removal conduit arrangement 39 is fluidically connected to the second outlet 34 of the membrane plant 28, it being possible to discharge permeate mixture from the second outlet 34 of the membrane plant 28 through the second membrane plant removal conduit arrangement 39 from the preparation plant 100.

In the embodiment of the present invention shown in FIG. 1, a formaldehyde source 40 is fluidically connected via a formaldehyde feed arrangement 41 to the second distillation column removal conduit arrangement 15, by means of which formaldehyde can be routed through the formaldehyde feed arrangement 41 into the second distillation column removal conduit arrangement 15, and further through the latter into the reactor 1. A propionaldehyde source 42 is fluidically connected via a propionaldehyde feed arrangement 43 to the second distillation column removal conduit arrangement 15, by means of which propionaldehyde can be routed from the propionaldehyde source 42 through the propionaldehyde feed arrangement 43 into the second distillation column removal conduit arrangement 15, and further through the latter into the reactor 1.

A base source 44 is fluidically connected via a base feed arrangement 45 to the second distillation column removal conduit arrangement 15, by means of which a base or bases can be routed through the base feed arrangement 45 into the second distillation column removal conduit arrangement 15, and further through the latter into the reactor 1. An acid source 48 is fluidically connected via an acid feed arrangement 47 to the second distillation column removal conduit arrangement 15, by means of which acid or acids can be routed through the acid feed arrangement 47 into the second distillation column removal conduit arrangement 15, and further through the latter into the reactor 1.

The preparation plant 100 can be used, for example, to perform the process described hereinafter for preparation of methacrolein from formaldehyde and propionaldehyde in the presence of water and a homogeneous catalyst based at least on an acid and a base.

Formaldehyde, propionaldehyde, water and homogeneous catalyst are introduced into the reactor 1 through the second section 30 of the second distillation column removal conduit arrangement 15. Fresh formaldehyde is introduced here from the formaldehyde source 40 via the formaldehyde feed arrangement 41 into the second section 30 of the second distillation column removal conduit arrangement 15, fresh propionaldehyde from the propionaldehyde source 42 via the propionaldehyde feed arrangement 43, one or more fresh bases from the base source 44 via the base feed arrangement 44, and one or more fresh acids from the acid source 46 via the acid feed arrangement 47. The formaldehyde, the acid or acids and the base or bases are each in an aqueous solution. i.e. these aqueous solutions introduce water. The acid or acids in conjunction with the base or bases are the homogeneous catalyst.

Suitable aqueous formaldehyde solutions are, for example, those having a content based on the total mass or the formaldehyde solution of 30% to 55% by weight of formaldehyde with a preferably low methanol content of, for example, 0.3% to 10% by weight, based on the total mass of the formaldehyde solution.

Propionaldehyde is available in highly concentrated form. For example, propionaldehyde feedstock mixture is available with a residual water content of 0.1% to 2.5% by weight, based on the total mass of the propionaldehyde feedstock mixture, and a propionic acid content of 0.01% to 1% by weight, based on the total mass of the propionaldehyde feedstock mixture.

Preference Is given to a slight excess of formaldehyde over propionaldehyde in the reactor input. Particular preference is given to choosing a molar ratio of propionaldehyde to formaldehyde in the reactor inlet in the range from 0.90 to 0.99, most preferably 0.95 to 0.98. In this way, it is firstly possible to achieve a good conversion with low formaldehyde consumption. Secondly, the catalyst is also protected at the same time. This is because excessively high formaldehyde contents promote the conversion of dimethylamine to trimethylamine.

Suitable acids are especially inorganic acids, organic monocarboxylic acids, organic dicarboxylic acids and organic polycarboxylic acids. Other organic acids are also usable in principle, but are not usually used for reasons of cost. Preference is given to using organic monocarboxylic acids.

Inorganic acids used may, for example, be sulfuric acid and/or phosphoric acid.

Of the organic monocarboxylic acids, preference is given to aliphatic organic monocarboxylic acids. Of the aliphatic monocarboxylic acids, preference is given to those having two to ten carbon atoms, particularly those having two, three or four carbon atoms.

Of the aliphatic di- and polycarboxylic acids, preference is given to those having two to ten carbon atoms, particularly those having two, four, five or six carbon atoms.

The organic dicarboxylic acids and the organic polycarboxylic acids may be aromatic, araliphatic and aliphatic carboxylic acids, preference being given to aliphatic di- and polycarboxylic acids.

For example, it is possible to use acetic acid, propionic acid, methoxyacetic acid, n-butyric acid, isobutyric acid, oxalic acid, succinic acid, tartaric acid, glutaric acid, adipic acid, maleic acid or fumaric acid, preference being given to acetic acid.

It is also possible to use mixtures of two or more acids.

Suitable bases are especially organic bases, preference being given to amines.

Of the amines, preference is given to secondary amines, particularly those or the formula $R^1R^2NH$ in which $R^1$ and $R^2$ are the same or different and may each denote:

an alkyl radical having one to ten carbon atoms, preferably one to eight carbon atoms, more preferably one to four carbon atoms, where the carbon atoms may also be substituted by ether, hydroxy or secondary or tertiary amine groups, preferably by one or two of these groups, an aralkyl radical having seven to twelve carbon atoms, a cycloalkyl radical having five to seven carbon atoms, together with the adjacent nitrogen members of a heterocyclic ring, preferably of a five- to seven-membered ring, that may also contain a further nitrogen atom and/or an oxygen atom and may be substituted by hydroxyalkyl or alkyl groups having one to four carbon atoms.

It is possible to use one or more bases.

Amines used may be, for example: dimethylamine, diethylamine, methylethylamine, methylpropylamine, dipropylamine, dibutylamine, diisopropylamine, diisobutylamine, methylisopropylamine, methylisobutylamine, methyl-sec-butylamine, methyl(2-methylpentyl)amine, methyl(2-ethylhexyl)amine, pyrrolidine, piperidine, morpholine, N-methylpiperazine, N-hydroxyethylpiperazine, piperazine, hexamethyleneimine, diethanolamine, methylethanolamine, methylcyclohexylamine, methylcyclopentylamine or dicyclohexylamine.

It is also possible to use mixtures of two or more bases.

If a mixture of amines is used, the amines are preferably selected such that at least one of the amines used does not have a hydroxy group. More preferably, the proportion of amines having at least one hydroxy group in the reactor is not more than 50% by weight, preferably not more than 30% by weight and more preferably not more than 10% by weight, based on the weight of amines used.

The proportion of acid or acids (in total) based on propionaldehyde in the reactor is preferably in the range from 0.1 to 20 mol %, more preferably in the range from 0.5 to 10 mol % and most preferably in the range from 1 to 5 mol %. In the case of too small an amount of acid—and hence too small an amount of catalyst—in the reactor, the reactor would have to be constructed quite large and operated quite hot. In the case of too large an amount of acid—and hence too large an amount of catalyst—the reactor would become quite hot.

It is advisable to have somewhat more acid compared to the base in the reactor. This is advantageous since the Mannich reaction requires protons. Acids can also bind bases. If, for example, the acid chosen is acetic acid and the base chosen is dimethylamine, the acetic acid binds the volatile dimethylamine. This prevents dimethylamine as volatile component from getting into the tops from the first distillation column 11.

If, for example, the acid chosen is acetic acid and the base dimethylamine, a molar ratio of acetic acid to dimethylamine in the range from 2.0 to 1.1 at the reactor inlet is of good suitability, particular preference being given to a molar ratio of acetic acid to dimethylamine of 1.1.

The proportion of the base or bases (in total) based on propionaldehyde in the reactor inlet is preferably in the range from 0.1 to 20 mol % based on moles of propionaldehyde at the reactor inlet, more preferably in the range from 0.5 to 15 mol % based on moles of propionaldehyde at the reactor inlet, and most preferably in the range from 1 to 10 mol % based on moles of propionaldehyde at the reactor inlet. If too small an amount of base or bases is used, the reaction is unselective and the reactor has to be operated at higher temperatures. If too large an amount of base or bases is used, the performance of the reaction becomes increasingly uneconomic, and the wastewater is found to be even more highly polluted.

If the base used is dimethylamine, for example, the molar ratio of dimethylamine to propionaldehyde in the reactor inlet is preferably in the range from 0.08 to 0.12, more preferably 0.08 to 0.1.

Preference Is given to a stoichiometric ratio of acid to base of greater than one in order to have sufficient acidity to cleave the Mannich base, especially when a volatile base able to efficiently bind the base is used, in order to be able to transfer it efficiently into the bottom 13 of the first distillation column and to be able to remove it from there.

In the reactor 1, a Mannich reaction takes place in the liquid phase, in which formaldehyde and propionaldehyde are converted to methacrolein in the presence of water and in the presence of the homogeneous catalyst.

The reaction temperature at the outlet or the reaction zone of reactor 1 is chosen such that it is preferably in the range from 100° C. to 210° C., more preferably in the range from 110° C. to 200° C., even more preferably in the range from 120° C. to 190° C. and very especially preferably in the range from 130° C. to 180° C. It is possible thereby to achieve a high conversion and a good yield.

The pressure in the reactor 1 is chosen at least at a sufficiently high level that the reaction mixture remains in liquid form in the reactor 1. With these provisions, an appropriate pressure is set in the reactor 1, which is preferably in the range from 15 to 100 bar, more preferably in the range from 18 to 80 bar, even more preferably in the range from 22 to 50 bar and very especially preferably in the range from 25 to 40 bar. The pressures are absolute pressures.

Even after the liquid reaction mixture has left the reaction zone of the reactor 1, the Mannich reaction and also other further reactions, for example conversion of methacrolein to dimethacrolein or methacrolein oligomerization, can still proceed to a considerable degree, especially when the reaction mixture is still under the pressure within the reaction zone, and essentially still has the temperature that it has on exiting from the reaction zone. The reaction residence time in the present context is understood to mean the average time that elapses between the entry of the reactants into the reaction zone of the reactor 1 and the commencement of expansion of the reaction mixture in the expansion valve 3. The dwell time in the reaction zone is preferably in the range from 0.001 minute to 25 minutes, more preferably in the range from 0.001 minute to 10 minutes, even more preferably in the range from 0.1 second to 300 seconds, very especially preferably in the range from 1 second to 50 seconds, even further preferably in the range from 5 to 20 seconds. It is possible thereby to efficiently limit side reactions and further reactions with a good yield.

The reaction mixture contains methacrolein and the accompanying components water, unconverted formaldehyde, unconverted propionaldehyde and catalyst. It may also contain one or more of the following further accompanying components:

methanol, if methanol was present in the fresh aqueous formaldehyde solution dimethacrolein trimethylamine, if dimethylamine is used as base high boilers, especially high-boiling aldolization products oligomers, especially oligomers of methacrolein stabilizer (e.g. Tempol)

dimers of propionaldehyde

The reaction mixture is routed to the expansion valve 3 by means of the reactor removal conduit arrangement 2 and, by means of the expansion valve 3, expanded to a desired pressure, for example to a pressure in the range from 500 mbar (absolute) to standard pressure. The pressure relief results in conversion of at least a portion of the reaction mixture from the liquid phase to the gaseous phase, which gives rise to a first expansion mixture, namely the fraction of the reaction mixture that is converted to the gas phase as a result of the expansion. The fraction of the reaction mixture remaining in the liquid phase after the expansion is a second expansion mixture.

Since the methacrolein-water azeotrope has a lower boiling point than water and is therefore more readily evaporated than water, the first expansion mixture contains a higher proportion of methacrolein than the second expansion mixture, it is quite possible here for more than 90% by weight of the methacrolein present in the reaction mixture overall to go into the first expansion mixture. In other words, the expanding by means of the expansion valve 3 is already a first step for purification of methacrolein.

The reduction in pressure and the conversion of a portion of the reaction mixture to the gaseous phase lead to a reduction in the temperature of the portion of the reaction mixture converted to the gas phase (first expansion mixture) and of the portion of the reaction mixture remaining in the liquid phase (second expansion mixture). Consequently, no other cooling is required for this cooling effect.

The process is preferably conducted in such a way that the first and second expansion mixtures after the expansion have a temperature in the range from about 60 to 120° C., preferably a temperature in the range from about 70 to 110° C. and more preferably a temperature in the range from about 80 to 90° C. it has been found that, in these temperature ranges, the extent of the unwanted side reactions and further reactions that can take place is less critical than was thought. More particularly, the first and second expansion mixtures can remain within the temperature ranges specified for a few minutes, preferably for 0.1 to 15 minutes, more preferably 1 to 5 minutes, even further preferably 0.5 to 3 minutes. These are dwell times of good acceptability with regard to unwanted side reactions and further reactions.

The dwell time of the first expansion mixture in the expansion vessel 5 is preferably lower than that of the second expansion mixture.

If the reaction mixture supplied to the expansion valve 3 is, for example, at a temperature of 165° C. and a pressure of 35 bar (absolute) and the composition based on its total mass contains 63.51% by weight of water and 29.04% by weight of methacrolein, a rapid expansion to 0.85 bar (absolute) can lead to a temperature of the first and second expansion mixtures of 78.9° C. (cf. first experimental example according to the invention).

The expansion valve removal conduit arrangement 4 routes the first expansion mixture and the second expansion mixture into the expansion vessel 5. In the expansion vessel 5, the first expansion mixture and the second expansion mixture are separated from one another.

The first expansion mixture is routed into the first condenser 9 via the first outlet 6 of the expansion vessel 5 and the first expansion vessel removal conduit arrangement 8. The second expansion mixture is routed into the first distillation column 11 via the second outlet 7 of the expansion vessel 5 and the second expansion vessel removal conduit arrangement 10.

Preferably, the expansion vessel 5 is operated in such a way that a good fill level of second expansion mixture is present therein, the dwell time of the second expansion mixture in the expansion vessel 5 being distinctly higher than the dwell time of the first expansion mixture.

The first expansion mixture is condensed in the first condenser 9.

In the first distillation column 11, the second expansion mixture is separated into a first distillation mixture and a second distillation mixture, the first distillation mixture being in the form of a gas phase at the top 12 of the first distillation column 11 and the second distillation mixture in the form of a liquid phase in the bottom 13 of the first distillation column 11. The first distillation mixture has a higher proportion by weight of methacrolein than the second distillation mixture. The first distillation mixture also contains unconverted propionaldehyde and unconverted formaldehyde. The second distillation mixture has a higher proportion by weight of water than the first distillation mixture. Moreover, the second distillation mixture contains at least the greater portion of the catalyst supplied by the second expansion mixture compared to the first distillation mixture. The second distillation mixture also contains unconverted formaldehyde.

It is possible to configure the process in the first distillation column 11 in such a way that virtually all the catalyst supplied by the second expansion mixture is present in the bottom 13 of the first distillation column 11.

The first distillation column 11 can be operated at standard pressure, for example, such that there is a temperature of somewhat above 100° C. in the bottom 13 thereof. The reason for the increase somewhat beyond 100° C. (for standard pressure) Is the catalyst content present in the bottom 13, as a result of which the boiling temperature of the second distillation mixture increases correspondingly.

The temperature at the top 12 of the first distillation column 11 at standard pressure may be chosen within the range from 68 to 98° C., preferably within the range from 80 to 90° C. This means that more water gets into the top 12 than at lower temperatures at the top 12.

The first distillation mixture is routed into the first condenser 9 via the first distillation column removal conduit arrangement 14 and likewise condensed therein. The condensate from the first condenser 9 contains an organic phase (first separation mixture) containing methacrolein, and an aqueous phase (second separation mixture).

The condensate from the first condenser 9 is routed into the first phase separator 18 via the condensate outlet 16 thereof and the condenser removal conduit arrangement 17. The organic phase and aqueous phase, i.e. first and second separation mixtures, are separated from one another therein. The organic phase, i.e. the first separation mixture, is removed via the first outlet 19 of the first phase separator 18 and the first phase separator removal conduit arrangement 21, for example into a tank or a further processing plant, for example a plant for preparation of methyl methacrylate. The aqueous phase, i.e. the second separation mixture, is routed via the second outlet 20 of the first phase separator 18 and the second phase separator removal conduit arrangement 22 into the second distillation column 23. The water content in the second separation mixture, based on the total mass of the second separation mixture, may quite possibly be 75% by weight or higher. The methacrolein content in the second separation mixture, based on the total mass of the second separation mixture, may quite possibly be in the range from 2% to 10% by weight. The methanol content in the second separation mixture, based on the total mass of the second separation mixture, may quite possibly be in the range from 1% to 10% by weight. The second separation mixture may also contain formaldehyde. It will be apparent that the totality or an constituents of the second separation mixture together makes up 100% by weight or the total mass of the second separation mixture.

By virtue of the second separation mixture being routed into the second distillation column 23 and not into the first distillation column 11 in this embodiment of the invention, less water gets into the first distillation column 11. As a result, the concentration of the catalyst in the bottom 13 of the first distillation column 11 is higher than if the second separation mixture were to be introduced into the first distillation column 11. Since the amount of water returnable to the reactor 1 is limited, the amount of the second distillation mixture returnable to the reactor 1 is also limited owing to the amount or water present therein. Since the second distillation mixture in the present embodiment of the invention contains a relatively high proportion of catalyst, a relatively large portion of this catalyst can be returned to the reactor 1. It is accordingly possible to save fresh catalyst.

Since the first distillation column 11 is supplied with less water, a smaller amount of second distillation mixture is also obtained. Thus, if second distillation mixture is to be disposed of, a smaller amount of second distillation mixture has to be disposed of.

The second separation mixture is separated in the second distillation column 23 into a third distillation mixture and a fourth distillation mixture, wherein the third distillation mixture is in the form of a gas phase at the top 24 of the second distillation column 23 and comprises methacrolein, and the fourth distillation mixture is in the form of a liquid phase at the bottom 25 of the second distillation column 23 and comprises water. Since the catalyst for the most part gets into the bottom 13 of the first distillation column 11, less catalyst correspondingly gets into the bottom 25 of the second distillation column 23. Accordingly, the fourth distillation mixture is less problematic in terms of its environmental properties than the second distillation mixture. Since it is possible to operate the first distillation column 11 in such a way that almost all the catalyst present in the second expansion mixture collects in the bottom 13 of the first distillation column 11, and since it is also additionally possible, with good effectiveness, to prevent drops and droplets of second expansion mixture in the expansion vessel 5 from leaving it via the first outlet 8 thereof, it is possible to obtain a fourth distillation mixture containing only a small amount of or barely any catalyst. It is thus possible to obtain a fourth distillation mixture which, with regard to the catalyst, causes little or barely any environmental pollution and can easily be disposed of in this regard, for example by releasing it into a communal water treatment plant.

The second distillation column 23 can be operated, for example, at standard pressure such that there is a temperature in the range from about 100 to 102° C. in its bottom 25, in order to promote passage of the low boilers, for example methanol and methacrolein, into the top 24 of the second distillation column.

The temperature at the top 24 of the second distillation column at standard pressure may be chosen within the range from 85 to 99° C. preferably in the range from 70 to 95° C. This promotes good depletion of low boilers in the wastewater.

For example, it is possible to obtain a third distillation mixture which, based on its total mass, contains more than 30% by weight of methacrolein and more than 40% by weight of water. As further components, it may contain methanol in particular.

It is possible here to obtain, for example, a fourth distillation mixture which, based on its total mass, contains more than 98% by weight of water and less than 1% by weight of methanol and has been very substantially freed of methacrolein.

The third distillation mixture is routed through the third distillation column removal conduit arrangement 26 from the top 24 of the second distillation column 23 into the first condenser 9 and condensed therein.

The fourth distillation mixture is discharged from the preparation plant via the fourth distillation column removal conduit arrangement 27 from the bottom 25 of the second distillation column 23. It can be collected in a tank or sent to a further processing plant, for example a preparation plant for preparation of methyl methacrylate, wherein the methacrolein present in the fourth distillation mixture is a reactant for preparation or methyl methacrylate.

The second distillation mixture is routed via the first section of the second distillation column removal conduit arrangement 15. Subsequently, the portion of the second distillation mixture that is to be routed to the reactor 1 is routed into the second section 30 of the second distillation column removal conduit arrangement 15 and hence to the reactor 1, the portion of the second distillation mixture that is to be routed out of the preparation plant 100 is routed into the third section 31 of the second distillation column removal conduit arrangement 15, and the portion of the second distillation mixture that is to be routed into the membrane plant 28 is routed into the fourth section 32 of the second distillation column removal conduit arrangement 15.

In the membrane plant 28, at least a portion of the catalyst present in the second distillation mixture is retained (retentate mixture). Accordingly, the retentate mixture has a higher concentration or catalyst than the second distillation mixture. The permeate mixture from the membrane plant 28 has a correspondingly lower proportion of catalyst. Accordingly, the permeate mixture, with regard to its catalyst content, is less environmentally polluting than the retentate mixture. With a correspondingly effective membrane plant, it is possible to obtain a permeate mixture having a sufficiently low catalyst concentration that the permeate mixture can be disposed of without any problem with regard to its catalyst concentration, for example by releasing it into a communal water treatment plant.

A preferred membrane plant is a reverse osmosis membrane plant.

The retentate mixture is routed via the first outlet 33 or the membrane plant 28 into the first section 38 of the first membrane plant removal conduit arrangement 35. The portion of the retentate mixture that is to be routed into the reactor 1 is routed through the second section 37 of the first membrane plant removal conduit arrangement 35 into the second section 30 of the second distillation column removal conduit arrangement 15. The portion of retentate mixture that is to be routed out of the preparation plant 100 is discharged from the preparation plant 100 through the third section 38 of the first membrane plant removal conduit arrangement 35.

Permeate mixture is removed from the preparation plant 100 via the second outlet 34 of the membrane plant 28 and the second membrane plant removal conduit arrangement 39.

If the permeate mixture contains a sufficiently small amount of catalyst, it can, at least with regard to its catalyst content, be released into a public water treatment plant for disposal.

If the aim is to dispose of catalyst, trimethylamine and/or unwanted high boilers present in the second distillation mixture, the disposal of retentate mixture is favourable than the direct disposal of second distillation mixture via the third section 31 of the second distillation column removal conduit arrangement 15 in that the retentate mixture contains less water based on the same amount of catalyst, trimethylamine and/or unwanted high boilers. If the disposal is to be effected, for example, by addition to an incineration, less energy is required for the disposal of retentate mixture since less water has to be concomitantly evaporated than if the same amount of catalyst, trimethylamine and/or unwanted high boilers were to be incinerated by adding second distillation mixture to the incineration.

The conversion of dimethylamine to trimethylamine increases the trimethylamine content in the second distillation mixture at the expense of the dimethylamine content through the recycling or second distillation mixture and/or retentate mixture to the reactor 1. Too great a decrease in dimethylamine in favour of trimethylamine correspondingly worsens the methacrolein yield in the reactor 1, or entails a corresponding increase in the reaction temperature in order to efficiently counter the drop in the methacrolein yield in the reactor 1. However, too high a reaction temperature promotes the formation of unwanted by-products. The amount of trimethylamine which is returned to the reactor 1 may especially be reduced by removing second distillation mixture via the third section 31 of the second distillation column removal conduit arrangement 15 and/or retentate mixture via the third section 38 of the first membrane plant removal conduit arrangement 35. Catalyst thus lost can be compensated for by the supplying of fresh catalyst to the reactor 1.

The amount of water that can be fed into the reactor 1 is limited. If the amount of water present in the second distillation mixture obtained is higher than the amount of water that can or should be recycled into the reactor 1, and therefore not all the second distillation mixture obtained can or should be recycled into the reactor 1, not all the catalyst present in the second distillation mixture obtained can be reused. The amount of the catalyst present in the second distillation mixture obtained that can be returned to the reactor 1 can be increased by reducing the amount of the second distillation mixture returned to the reactor 1 and increasing the amount of the retentate mixture introduced into the reactor 1.

The mixture or mixtures introduced Into the second section 30 of the second distillation column removal conduit arrangement 15 from the first section 29 of the second distillation column removal conduit arrangement 15 and/or the second section 37 of the membrane plant removal conduit arrangement 35 especially return unconverted formaldehyde, water and catalyst to the reactor 1.

The reactor 1 can be supplied with fresh catalyst by routing an appropriate amount of acid or acids and bases or bases from the acid source 46 and base source 44 into the reactor 1.

The formaldehyde and propionaldehyde reactants are fed to the reactor 1 from the formaldehyde source 30 and the propionaldehyde source 42.

Reference is made to FIG. 2. The inventive preparation plant 200 of the second embodiment of the invention, illustrated schematically in a flow diagram therein, differs only partially from the preparation plant 100 of the first embodiment of the invention. Solely differences are addressed hereinafter.

By contrast with the preparation plant 100 of the first embodiment of the invention, the preparation plant 200 of the second embodiment additionally has a second condenser 51. A third distillation column removal conduit arrangement 50 is provided, which, by contrast with the third distillation column removal conduit arrangement 26 of the first embodiment of the invention, fluidically connects the top 24 of the second distillation column 23 not to the first condenser 9 but to the second condenser 51, it being possible to route third distillation mixture from the top 24 of the second distillation column 23 through the third distillation column removal conduit arrangement 50 of the second embodiment of the invention into the second condenser 51. The third distillation mixture can be condensed in the second condenser 51. The second condenser 51 has a condensate outlet 52 fluidically connected by a second condenser removal conduit arrangement 53 to the first phase separator 18, it being possible to route condensate from the second condenser 51 through the second condenser removal conduit arrangement 53 from the second condenser 51 into the first phase separator 18.

The second condenser 51 can condense the third distillation mixture independently of the first condenser 9. Since the second condenser 51 is fluidically connected to the first phase separator 18, the first phase separator 18 can also be utilized for further workup of the condensate from the second condenser 51. In other words, no second phase separator is needed.

Reference is made to FIG. 3. The preparation plant 300 of the third embodiment of the invention, illustrated schematically in a flow diagram therein, differs only partially from the preparation plant 200 of the second embodiment of the invention. Solely differences are elucidated hereinafter.

By contrast with the preparation plant 200 of the second embodiment of the invention shown in FIG. 2, the preparation plant 300 of the third embodiment of the invention additionally has a second phase separator 81 with which an organic phase (third separation mixture) present in the condensate of the second condenser 51 can be separated from an aqueous phase (fourth separation mixture) present in the condensate of the second condenser 51. A second condenser removal conduit arrangement 60 is provided here, which fluidically connects the condensate outlet 52 of the second condenser 51 to the second phase separator 61 rather than to the first phase separator 18, by means of which it is possible to route condensate from the second condenser 51 from the second condenser 51 through the second condenser removal conduit arrangement 80 into the second phase separator 61. The second phase separator 61 has a first outlet 62 for removal of the organic phase separated off, i.e. for removal of third separation mixture, and a second outlet 63 for removal of the aqueous phase, i.e. for removal of fourth separation mixture. The first outlet 62 of the second phase separator 61 is fluidically connected to the first phase separator removal conduit arrangement 21 by a third phase separator removal conduit arrangement 64, by means of which third separation mixture can be introduced through the third phase separator removal conduit arrangement 64 into the first phase separator removal conduit arrangement 21 and can be removed together with first separation mixture through the section of the first phase separator removal conduit arrangement 21 adjoining the discharge site on the downstream side.

Condensate from the second condenser 51 is routed into the second phase separator 61. Third and fourth separation mixture are separated therein, with the third separation mixture containing more methacrolein than the fourth separation mixture and the fourth separation mixture containing more water than the third separation mixture. The third separation mixture, just like the first separation mixture, has a good methacrolein content and can be used for further processing, for example for preparation of methylmethacrolein.

In the third embodiment of the invention, the third separation mixture is routed through the third phase separator removal conduit arrangement 64 and through the section of the first phase separator removal conduit arrangement 21 adjoining the discharge site on the downstream side. In other words, in the third embodiment of the invention, first and third separation mixture are combined.

The second outlet 63 of the second phase separator 61 is fluidically connected to the second distillation column 23 by a fourth phase separator removal conduit arrangement 65, it being possible to route fourth separation mixture through the fourth phase separator removal conduit arrangement 65 from the second phase separator 61 into the second distillation column 23. Through the introduction of fourth separation mixture into the second distillation column 23, it is possible to separate methacrolein present in the fourth separation mixture from water present in the fourth separation mixture.

Reference is made to FIG. 4. The fourth embodiment of the invention Illustrated schematically in FIG. 4 differs only partially from the first embodiment of the invention shown in FIG. 1. Solely differences of the fourth embodiment of the invention from the first embodiment of the invention are elucidated hereinafter.

In the preparation plant 400 of the fourth embodiment of the invention, a third distillation column removal conduit arrangement 70 is provided, which fluidically connects the top 24 of the second distillation column 23 to the first distillation column 11 of the fourth embodiment of the invention rather than to the first condenser 9, it being possible to route third distillation mixture from the top 24 of the second distillation column 23 through the third distillation column removal conduit arrangement 70 into the first distillation column 11. Through the introduction of third distillation mixture into the first distillation column 11, the third distillation mixture is supplied to the appropriate further workup. The third distillation mixture does also contain water. However, the associated input of water into the first distillation column 11 is manageable and is much smaller than if second separation mixture were to be introduced into the first distillation column 11. The advantages that are achieved thereby, that the second separation mixture is introduced not into the first distillation column 11 but into the second distillation column 23, are maintained to a good degree.

Reference is made to FIG. 5. The fifth embodiment of the invention differs only partially from the fourth embodiment of the invention. Solely differences are addressed hereinafter.

In the preparation plant 500 of the fifth embodiment of the invention, by contrast with the preparation plant 400 of the fourth embodiment of the invention, a third distillation column removal conduit arrangement 80 is provided, which connects the top 24 of the third distillation column 23 to the expansion vessel 5 rather than to the first distillation column 11. This third distillation column removal conduit arrangement 80 can route third distillation mixture from the top 24 of the second distillation column 23 into the expansion vessel 5. Through the introduction of third distillation mixture into the expansion vessel 5, the third distillation mixture is supplied to the appropriate further workup. More particularly, the third distillation mixture, since it is gaseous, flows together with the first expansion mixture through the first expansion vessel removal conduit arrangement 8 into the first condenser 9 and is condensed therein. As part of the condensate of the first condenser 9, the condensed third distillation mixture is routed through the first condenser removal conduit arrangement 17 into the first phase separator 18 and passes through the separation process therein.

Further possible variations that can be implemented individually or in any desired combinations are described hereinafter.

Preparation plants that combine more than one or al of the first, second, third, fourth and fifth embodiments with one another are possible.

Individual or all distillation columns may have a reboiler circuit through which respective bottoms mixture is routed and in which this is heated.

Individual or all distillation columns may have a separate condenser circuit with which tops mixture is condensed and fed back into the distillation column in question, wherein the separate condenser circuit has a dedicated condenser.

It is also possible to utilize the first condenser 9 as well for the condensing of the tops mixture from the first distillation column; in other words, no separate condenser would be required in this case. It is additionally possible to utilize the respective second condenser 51 as well for the condensing of the tops mixture from the second distillation columns of the second and/or third embodiments of the invention; in other words, in this case too, no separate condenser would be required.

Individual or all distillation columns may each have a droplet retaining unit with which drops and droplets can be prevented from leaving the distillation column in question via the top thereof. The droplet retaining unit may take the form, for example, of a fine-mesh sieve, of what is called a demister, or of a liquid release unit with which liquid is released within the distillation column in the direction of the bottom of the distillation column in question, where this liquid collects ascending drops and droplets, by means of which the liquid of the drops and droplets is then moved in the direction of the bottom. The droplet retention unit increases the separating efficiency of the distillation column in question.

The second distillation column 23 may be a packed column or a tray column or a mixed form thereof.

Individual or all distillation columns may contain random packings and/or structured packings.

One or more of the condensers 9, 51 may have a ventilation via which offgas from one or more reactions can be removed.

One or more of the condensers 9, 51 may be in multistage form, for example in two-stage form. In the two-stage case, it would be possible with the first condenser stage, for example, to achieve cooing to about 30 to 40° C., and with the second condenser stage, for example, cooling to about 3 to 10° C., preferably to 4° C. Multistage operation saves cooling brine.

If multistage condensers are used, it is possible to recycle a portion of the condensate into the first condensation stage and add a stabilizer that acts against polymerization.

One or more of the condensers 9, 51 may have a gas phase removal unit with which any gas phase present in the condenser in question can be removed from this condenser.

Second separation mixture can be admixed with an agent that counteracts polymerization, for example the polymerization of methacrolein and/or of dimethylamine. This modified second separation mixture can be introduced into one or more condensers in order to counteract polymerization even therein.

The substances introduced into the reactor 1 may be preheated, for example, to a temperature of about 130° C.

The reactor 1 may take the form of a tubular reactor.

The base or bases introduced into the reactor 1 from the base source 44, acid or acids from the acid source 48 and/or the recycle stream which is introduced into the reactor 1 through the second section 30 of the second distillation column removal conduit arrangement 15 coming from the first section 29 of the second distillation column removal conduit arrangement 15 and/or the second section 37 of the first membrane plant removal conduit arrangement 35 can be more significantly preheated than the fresh formaldehyde and the fresh propionaldehyde that are introduced into the reactor 1 from the formaldehyde source 40 and the propionaldehyde source 42. It is possible here to heat the acid or acids, the base or bases and/or the recycle stream mentioned to such a degree that a desired premixing temperature is attained only after mixing thereof with the fresh formaldehyde and the fresh propionaldehyde. In this way, the fresh formaldehyde and the fresh propionaldehyde remain for longer at a temperature lower than the desired premixing temperature. The recycled material mentioned can also be preheated.

Heat can be removed from the second distillation mixture removed from the bottom 13 of the first distillation column 11, and can be utilized at least partly for preheating of at least a portion of the substances introduced into the reactor 1.

Individual or all expansion vessels 5 may have a droplet retaining unit with which drops and droplets of second expansion mixture can be prevented from leaving the expansion vessel 5 via the first outlet 6 thereof together with first expansion mixture. The droplet retaining unit may take the form, for example, of a fine-mesh sieve. The droplet retaining unit increases the separation efficiency of the expansion vessel 5. Accordingly, the amount of catalyst that leaves the expansion vessel 5 via the first outlet 6 thereof is also reduced.

The droplet retaining unit of the expansion vessel 5 may take the form of a "demister".

The expansion vessel 5 may have a spraying unit with which the droplet retention unit can be sprayed from beneath with a liquid in order to increase the effect of the droplet retaining unit. The liquid may, for example, be second expansion mixture or a liquid containing an agent that counteracts the polymerization of methacrolein and/or dimethylamine.

If required, for example, stabilizer can be added to the first condenser 9 and/or the second section 30 of the second distillation column removal conduit arrangement 15.

In the first to fifth embodiments of the invention, the expansion valve 3, as shown in FIGS. 1 to 5, is disposed outside the expansion vessel 5. However, it is also possible to dispose the expansion valve 3 within the expansion vessel 5 or to integrate it into the wall thereof. In such cases, there are also possible configurations in which it is possible to dispense with an expansion valve removal conduit arrangement.

In the first to fifth embodiments of the invention, the first expansion vessel removal conduit arrangement 8 and the first distillation column removal conduit arrangement 14 lead separately into the first condenser 9. However, it is also possible that the first expansion vessel removal conduit arrangement 8 and the first distillation column removal conduit arrangement 14 are combined and are connected to a common inlet of the first condenser 9 in combined form, i.e. fluidically connected to this common inlet.

In the first embodiment of the invention, the third distillation column removal conduit arrangement 26 leads separately into the first condenser. However, it is also possible that the third distillation column removal conduit arrangement 28 and the first distillation column removal conduit arrangement 14 are combined and are connected to a common inlet of the first condenser 9 in combined form. i.e. fluidically connected to this common inlet.

In the first to fifth embodiments of the invention, a second distillation column removal conduit arrangement 15 is provided. However, it is also possible to provide two separate second distillation column removal conduit arrangements, wherein one has the first and second and optionally third sections 29, 30, 31 of the second distillation column removal conduit arrangements 15 of the first to fifth embodiments of the invention and consequently fluidically connects the bottom 13 of the first distillation column 11 especially to the reactor 1, and the other fluidically connect the bottom 13 of the first distillation column 11 to the membrane plant 28.

In the second and third embodiments of the invention, the third distillation column removal conduit arrangement 50 connects the top 24 of the second distillation column 23 to the second condenser 51 only. It is also possible to provide a third distillation column removal conduit arrangement that fluidically connects the top 24 of the second distillation column 23 both to the first condenser 9 and to the second condenser 51.

In the third embodiment of the invention, first and third separation mixture are combined. However, it is also possible to provide the third phase separator removal conduit arrangement in such a way that it is not fluidically connected to the first phase separator removal conduit arrangement 21 but is fluidically connected to a tank or a further processing plant separately therefrom.

The membrane plant 28 is always optional and can be omitted.

The membrane plant 28 may be in one-stage or multistage form.

The membrane plant is preferably a three-stage reverse osmosis membrane plant, the first stage of which is operated within a pressure range from 80 to 120 bar (absolute), the second stage of which is operated within a pressure range from 20 to 80 bar (absolute), and the third stage of which is operated within a pressure range from 20 to 40 bar (absolute). When the base used is dimethylamine and the acid used acetic acid, it is possible with a reverse osmosis membrane plant was operated to retain more than 99% of the dimethylamine present in the second distillation mixture, about 80% of acetic acid present in the second distillation mixture, and about 70% to 80% of the formaldehyde present in the second distillation mixture.

The membrane plant 28 may be provided with a cooling apparatus with which the working temperature in particular of the membrane plant can be regulated.

In the first to fifth embodiments of the invention, the formaldehyde reed arrangement 41, the propionaldehyde feed arrangement 43, the base feed arrangement 45 and the acid feed arrangement 47 are fluidically connected to the second section 30 of the second distillation column removal conduit arrangement 15. Alternatively, it is possible to fluidically connect the formaldehyde feed arrangement 41, the propionaldehyde feed arrangement 43, the base feed arrangement 45 and/or the acid feed arrangement 47 directly to the reactor 1, by means of which formaldehyde, propionaldehyde, base(s) and/or acid(s) can be introduced directly into the reactor 1.

In the first to fifth embodiments of the invention, fresh formaldehyde, fresh propionaldehyde, fresh acid or acids and fresh base or bases are supplied from separate sources. It is also possible to
premix fresh formaldehyde and fresh propionaldehyde or supply a mixture with formaldehyde and propionaldehyde from an appropriate source and/or
premix fresh acid or acids and fresh base or bases or supply a mixture with acid or acids and base or bases from an appropriate source.

If there is no premixing of acid or acids and base or bases, it is firstly possible to route acid or acids into the second section 30 of the second distillation column removal conduit arrangement 15, before base or bases are routed into the second section 30 of the second distillation column removal conduit arrangement 15. With this sequence, it is more easily possible to counteract a local excess of base.

The first phase separator 18 may be fluidically connected to the first distillation column 11, for example via a phase separator removal conduit arrangement that fluidically connects the second outlet 20 of the first phase separator 18 to the first distillation column 11, it being possible to route second separation mixture through this phase separator removal conduit arrangement from the second outlet 20 of the first phase separator 18 into the first distillation column 11.

The second phase separator 61, if present, may be fluidically connected to the first distillation column 11, for example via a phase separator removal conduit arrangement that fluidically connects the second outlet 63 of the second phase separator 61 to the first distillation column 11, it being possible to route fourth separation mixture through this phase separator removal conduit arrangement from the second outlet 63 of the first phase separator 81 into the first distillation column 11.

The second distillation column 23 may be omitted. In this case, the second phase separator removal conduit arrangement fluidically connects the first phase separator 18 to the first distillation column 11, it being possible to route second separation mixture through the second phase separator removal conduit arrangement from the second outlet 20 of the first phase separator 18 into the first distillation column 11. If a second phase separator is also provided, the fourth phase separator removal conduit arrangement may fluidically connect the second outlet 63 of the second phase separator 61 to the first distillation column 11, it being possible to route fourth separation mixture through the fourth phase separator removal conduit arrangement from the second outlet 63 of the second phase separator 61 into the first distillation column 11.

First Inventive Experimental Example

The Aspen Plus V8.8 simulation program from Aspen Technologies, Inc. was used to simulate the inventive operation of a first preparation plant according to the invention, apart from the variations enumerated hereinafter according to the first embodiment of the invention, but using the reference numerals of the first embodiment of the invention hereinafter in spite of these variations:

The preparation plant does not have a membrane plant.
The formaldehyde feed arrangement and the propionaldehyde feed arrangement are combined to form a formaldehyde-propionaldehyde feed arrangement that opens into the second section 30 of the second distillation column removal conduit arrangement 15.
The first condenser 9 has a gas phase removal unit fluidically connected to an incineration plant for incineration or the gas phase.
The first condenser 9 has a droplet retaining unit arranged upstream of its first outlet 6, in the form of a "demister".
The first condenser 9 has a collective inlet that combines the feed streams of first expansion mixture, first distillation mixture and third distillation mixture.
The first condenser 9 is in two-stage form.

From the bottom 13 of the first distillation column 11, recycle stream flows through the second section 30 of the second distillation column removal conduit arrangement 15 in the direction of the reactor 1. From the acid source 44, aqueous acetic acid solution is introduced via the acid feed arrangement 45 into the second section 30 of the second distillation column removal conduit arrangement 15. From the base source 46, aqueous dimethylamine solution is introduced via the base feed arrangement 47 into the second section 30 of the second distillation column removal conduit arrangement 15. The resultant mixture is preheated to 130° C.

Coming from the formaldehyde source 40, aqueous formaldehyde solution is introduced via the formaldehyde feed arrangement 41 into the formaldehyde-propionaldehyde feed arrangement and, from the propionaldehyde source 42, aqueous propionaldehyde solution is introduced via the propionaldehyde feed arrangement 43 into the formaldehyde-propionaldehyde feed arrangement.

The resultant mixture of formaldehyde and propionaldehyde solution is preheated to 130° C. and introduced into the second section 30 of the second distillation column removal conduit arrangement 15.

The mixture now present in the second section 30 of the second distillation column removal conduit arrangement 15 is introduced into the reactor 1 which, in this inventive experimental example, takes the form of a tubular reactor.

The dwell time in reactor 1 is 9.5 s, and the pressure in the reactor is 35 bar (absolute). Virtually fun conversion is achieved. The reaction mixture leaving the reactor has a temperature of 165° C. In the expansion vessel 5, the reaction mixture is expanded to 0.85 bar (absolute).

The first stage of the first condenser 9 is cooled with cooling water, and the second stage with cooing brine at a temperature of 4° C.

The gas phase present in the first condenser is sent to incineration via the gas phase removal unit.

Table 1 below reports the mass flow rate, the pressure, the temperature and the composition of some streams in the first inventive experimental example. In Table 1,
"Stream A" means: dimethylamine solution stream through the base feed arrangement 47,
"Stream B" means: acetic acid solution stream through the acid feed arrangement 45,
"Stream C" means: propionaldehyde solution stream through the propionaldehyde feed arrangement 43, "Stream D" means: formaldehyde solution stream through the formaldehyde feed arrangement 41,
"Stream E" means: stream entering reactor 1,
"Stream F" means: reaction mixture stream through the reactor removal conduit arrangement 2,
"Stream G" means: stream of first expansion mixture through the first expansion vessel removal conduit arrangement 8,
"Stream H" means: stream of second expansion mixture through the second expansion vessel removal conduit arrangement 10,
"Stream I" means: stream of first distillation mixture through the first distillation column removal conduit arrangement 14,
"Stream J" means: stream of second distillation mixture through the first section 29 of the second distillation column removal conduit arrangement 15,
"Stream K" means: stream of second distillation mixture which flows from the first section 29 or the second distillation column removal conduit arrangement 15 into the second section 30 of the second distillation column removal conduit arrangement 15,
"Stream L" means: stream of second distillation mixture which flows from the first section 29 of the second distillation column removal conduit arrangement 15 into the third section 31 of the second distillation column removal conduit arrangement 15 and is sent to a disposal.
"Stream M" means: stream through the collective inlet of the first condenser 9,
"Stream N" means: stream of first separation mixture through the first phase separator removal conduit arrangement 21,
"Stream O" means: stream of second separation mixture through the second phase separator removal conduit arrangement 22,
"Stream P" means: stream of third distillation mixture through the third distillation column removal conduit arrangement 26,
"Stream Q" means: stream of fourth distillation mixture through the fourth distillation column removal conduit arrangement 27,
the unit "%" represents % by weight based on the total mass of the stream in question and
the number of decimal places represents the accuracy of the numerical values.

TABLE 1

|  | Conditions | | | Composition | | | |
| --- | --- | --- | --- | --- | --- | --- | --- |
|  | Mass flow rate in kg/h | Temperature in ° C. | Pressure in bar (absolute) | Formaldehyde | Water | Methanol | Dimethacrolein |
| Stream A | 361 | 30.0 | 1.01 | 0.00% | 60.00% | 0.00% | 0.00% |
| Stream B | 264 | 30.0 | 1.01 | 0.00% | 20.00% | 0.00% | 0.00% |
| Stream C | 11159 | 30.0 | 1.01 | 0.00% | 2.50% | 0.00% | 0.00% |
| Stream D | 10388 | 65.0 | 1.01 | 55.00% | 44.50% | 0.50% | 0.00% |
| Stream E | 44321 | 130.0 | 36.00 | 13.43% | 56.00% | 0.21% | 0.01% |
| Stream F | 44321 | 165.0 | 35.00 | 0.72% | 63.51% | 0.23% | 0.19% |
| Stream G | 16136 | 78.9 | 0.85 | 0.12% | 21.79% | 0.32% | 0.46% |
| Stream H | 28184 | 78.9 | 0.85 | 1.06% | 87.40% | 0.18% | 0.03% |
| Stream I | 573 | 78.4 | 0.80 | 0.13% | 23.29% | 0.34% | 0.48% |
| Stream J | 27614 | 94.7 | 0.83 | 1.08% | 88.72% | 0.18% | 0.02% |
| Stream K | 22148 | 94.7 | 0.83 | 1.08% | 88.72% | 0.18% | 0.02% |
| Stream L | 5466 | 94.7 | 0.83 | 1.08% | 88.72% | 0.18% | 0.02% |
| Stream M | 17442 | 79.5 | 0.80 | 0.12% | 22.89% | 0.93% | 0.45% |
| Stream N | 13242 | 20.0 | 0.72 | 0.07% | 1.65% | 0.38% | 0.58% |
| Stream O | 4199 | 20.0 | 0.72 | 0.28% | 90.34% | 2.69% | 0.01% |
| Stream P | 732 | 91.4 | 1.00 | 0.12% | 46.89% | 14.98% | 0.06% |
| Stream Q | 3467 | 99.6 | 1.00 | 0.31% | 99.52% | 0.09% | 0.00% |

| | Composition | | | | | |
| --- | --- | --- | --- | --- | --- | --- |
|  | Propionaldehyde | Methacrolein | Acetic acid | Dimethylamine | Remainder | Trimethylamine |
| Stream A | 0.00% | 0.00% | 0.00% | 40.00% | 0.00% | 0.00% |
| Stream B | 0.00% | 0.00% | 80.00% | 0.00% | 0.00% | 0.00% |
| Stream C | 97.30% | 0.00% | 0.00% | 0.00% | 0.20% | 0.00% |
| Stream D | 0.00% | 0.00% | 0.00% | 0.00% | 0.00% | 0.00% |
| Stream E | 24.50% | 0.01% | 2.36% | 1.52% | 1.80% | 0.16% |
| Stream F | 0.02% | 29.04% | 2.36% | 1.49% | 2.25% | 0.20% |
| Stream G | 0.04% | 77.06% | 0.03% | 0.00% | 0.17% | 0.00% |
| Stream H | 0.00% | 1.54% | 3.69% | 2.34% | 3.43% | 0.32% |
| Stream I | 0.04% | 75.10% | 0.03% | 0.00% | 0.60% | 0.00% |
| Stream J | 0.00% | 0.02% | 3.77% | 2.39% | 3.49% | 0.32% |
| Stream K | 0.00% | 0.02% | 3.77% | 2.39% | 3.49% | 0.32% |
| Stream L | 0.00% | 0.02% | 3.77% | 2.39% | 3.49% | 0.32% |
| Stream M | 0.04% | 75.35% | 0.03% | 0.00% | 0.19% | 0.00% |
| Stream N | 0.05% | 97.13% | 0.03% | 0.00% | 0.12% | 0.00% |
| Stream O | 0.00% | 6.58% | 0.04% | 0.00% | 0.06% | 0.00% |
| Stream P | 0.02% | 37.72% | 0.04% | 0.00% | 0.17% | 0.00% |
| Stream Q | 0.00% | 0.00% | 0.04% | 0.00% | 0.04% | 0.00% |

It is apparent from Table 1 that the stream of first expansion mixture (stream G) has a high methacrolein content at 77.06% by weight and, by contrast, the stream of second expansion mixture (stream H) has a low methacrolein content at 1.54% by weight. The separation performance of the expansion vessel is thus high.

Moreover, it is apparent from Table 1 that the stream of first expansion mixture (stream G) has a mass flow rate of 16 136 kg/h. This large mass flow rate is routed into the first condenser 9. Thus, it need not be processed by the first distillation column 11.

Moreover, it is apparent from Table 1 that the methacrolein content of the stream of first expansion mixture (stream G) may be higher than that of the stream of first distillation mixture (stream I), which is 75.10% by weight in the first inventive experimental example.

Second Inventive Experimental Example

The Aspen Plus V8.8 simulation program from Aspen Technologies. Inc. was used to simulate the inventive operation of a second preparation plant according to the invention. By contrast with the first inventive experimental example, the preparation plant of the second inventive experimental example does not have a second distillation column, and the second phase separator removal conduit arrangement is fluidically connected to the first distillation column. The preparation process of the second inventive experimental example accordingly varies from the preparation process or the first inventive experimental example. In spite of these modifications, the reference numerals of the first embodiment of the invention are used hereinafter.

Table 2 below reports the mass flow rate, the pressure, the temperature and the composition of some streams in the second inventive experimental example. In Table 2, "Stream A" means: dimethylamine solution stream through the base feed arrangement 47.

"Stream B" means: acetic acid solution stream through the acid feed arrangement 45.

"Stream C" means: propionaldehyde solution stream through the propionaldehyde feed arrangement 43, "Stream D" means: formaldehyde solution stream through the formaldehyde feed arrangement 41, "Stream E" means: stream entering reactor 1, "Stream F" means: reaction mixture stream through the reactor removal conduit arrangement 2, "Stream G" means: stream of first expansion mixture through the first expansion vessel removal conduit arrangement 8, "Stream H" means: stream of second expansion mixture through the second expansion vessel removal conduit arrangement 10, "Stream I" means: stream of first distillation mixture through the first distillation column removal conduit arrangement 14, "Stream J" means: stream of second distillation mixture through the first section 29 of the second distillation column removal conduit arrangement 15, "Stream K" means: stream of second distillation mixture which flows from the first section 29 of the second distillation column removal conduit arrangement 15 into the second section 30 of the second distillation column removal conduit arrangement 15, "Stream L" means: stream of second distillation mixture which flows from the first section 29 of the second distillation column removal conduit arrangement 15 into the third section 31 of the second distillation column removal conduit arrangement 15 and is sent to a disposal.

"Stream M" means: stream through the collective inlet of the first condenser 9, "Stream N" means: stream of first separation mixture through the first phase separator removal conduit arrangement 21, "Stream O" means: stream of second separation mixture through the second phase separator removal conduit arrangement 22, the unit "%" represents % by weight based on the total mass of the stream in question and the number of decimal places represents the accuracy of the numerical values.

TABLE 2

| | Conditions | | | Composition | | | |
|---|---|---|---|---|---|---|---|
| | Mass flow rate in kg/h | Temperature in °C. | Pressure in bar (absolute) | Formaldehyde | Water | Methanol | Dimethacrolein |
| Stream A | 544 | 30.0 | 1.01 | 0.00% | 60.00% | 0.00% | 0.00% |
| Stream B | 398 | 30.0 | 1.01 | 0.00% | 20.00% | 0.00% | 0.00% |
| Stream C | 11159 | 30.0 | 1.01 | 0.00% | 2.50% | 0.00% | 0.00% |
| Stream D | 10388 | 65.0 | 1.01 | 55.00% | 44.50% | 0.50% | 0.00% |
| Stream E | 43232 | 130.0 | 36.00 | 13.55% | 56.00% | 0.26% | 0.00% |
| Stream F | 43232 | 165.0 | 35.00 | 0.52% | 63.70% | 0.29% | 0.18% |
| Stream G | 16044 | 78.5 | 0.85 | 0.08% | 21.26% | 0.39% | 0.44% |
| Stream H | 27188 | 78.5 | 0.85 | 0.77% | 88.74% | 0.23% | 0.03% |
| Stream I | 1168 | 79.0 | 0.80 | 1.56% | 35.33% | 4.37% | 0.71% |
| Stream J | 30002 | 94.7 | 0.83 | 0.70% | 91.13% | 0.29% | 0.00% |
| Stream K | 20742 | 94.7 | 0.83 | 0.70% | 91.13% | 0.29% | 0.00% |
| Stream L | 9260 | 94.7 | 0.83 | 0.70% | 91.13% | 0.29% | 0.00% |
| Stream M | 17319 | 77.1 | 0.80 | 0.19% | 22.64% | 0.67% | 0.46% |
| Stream N | 13232 | 20.0 | 0.72 | 0.11% | 1.63% | 0.27% | 0.59% |
| Stream O | 4087 | 20.0 | 0.72 | 0.43% | 91.13% | 1.95% | 0.01% |

TABLE 2-continued

| | Composition | | | | | |
|---|---|---|---|---|---|---|
| | Propionaldehyde | Methacrolein | Acetic acid | Dimethylamine | Remainder | Trimethylamine |
| Stream A | 0.00% | 0.00% | 0.00% | 40.00% | 0.00% | 0.00% |
| Stream B | 0.00% | 0.00% | 80.00% | 0.00% | 0.00% | 0.00% |
| Stream C | 97.30% | 0.00% | 0.00% | 0.00% | 0.20% | 0.00% |
| Stream D | 0.00% | 0.00% | 0.00% | 0.00% | 0.00% | 0.00% |
| Stream E | 25.12% | 0.01% | 2.37% | 1.56% | 1.06% | 0.09% |
| Stream F | 0.02% | 29.76% | 2.36% | 1.53% | 1.52% | 0.13% |
| Stream G | 0.04% | 77.59% | 0.03% | 0.00% | 0.16% | 0.00% |
| Stream H | 0.00% | 1.54% | 3.74% | 2.43% | 2.32% | 0.21% |
| Stream I | 0.04% | 57.50% | 0.02% | 0.00% | 0.47% | 0.00% |
| Stream J | 0.00% | 0.00% | 3.39% | 2.20% | 2.10% | 0.19% |
| Stream K | 0.00% | 0.00% | 3.40% | 2.20% | 2.09% | 0.19% |
| Stream L | 0.00% | 0.00% | 3.40% | 2.20% | 2.09% | 0.19% |
| Stream M | 0.04% | 75.80% | 0.03% | 0.00% | 0.18% | 0.00% |
| Stream N | 0.05% | 97.21% | 0.03% | 0.00% | 0.10% | 0.00% |
| Stream O | 0.00% | 6.39% | 0.04% | 0.00% | 0.05% | 0.00% |

It Is apparent from Table 2 that the stream of first expansion mixture (stream G) has a high methacrolein content at 77.59% by weight and, by contrast, the stream of second expansion mixture (stream H) has a low methacrolein content at 1.54% by weight. The separation performance of the expansion vessel is thus high in the second inventive experimental example too.

Moreover, it is apparent from Table 2 that the stream of first expansion mixture (stream G) has a mass flow rate of 16 044 kg/h. This large mass flow rate is routed into the first condenser 9. Thus, it need not be processed by the first distillation column 11.

Moreover, it is apparent from Table 2 that the methacrolein content of the stream of first expansion mixture (stream G) may actually be distinctly higher than that of the stream of first distillation mixture (stream I), which is 57.50% by weight in the second inventive experimental example.

The invention claimed is:

1. A process for preparing methacrolein from formaldehyde and propionaldehyde in the presence of a homogeneous catalyst mixture based at least on an acid and a base, the process comprising:
   S1: introducing formaldehyde, propionaldehyde and the homogeneous catalyst mixture based at least on the acid and the base into a reactor,
   S2: producing a liquid reaction mixture in the reactor under elevated pressure, wherein the reaction mixture comprises methacrolein and accompanying components, wherein the accompanying components comprise water, the homogenous catalyst mixture, unconverted formaldehyde, and unconverted propionaldehyde,
   S3: expanding the reaction mixture, which gives rise to a first expansion mixture which is a fraction of the reaction mixture that goes into a gas phase as a result of the expansion, and a second expansion mixture which is a fraction of the reaction mixture that remains in a liquid phase,
   S4: separating the first expansion mixture and the second expansion mixture in an expansion vessel,
   S5: introducing the first expansion mixture into a first condenser and condensing the first expansion mixture in the first condenser,
   S6: introducing the second expansion mixture into a first distillation column and separating the second expansion mixture introduced at least into a first distillation mixture and a second distillation mixture, wherein the first distillation mixture is in a form of a gas phase at the top of the first distillation column and comprises methacrolein, and the second distillation mixture is in a form of a liquid phase at the bottom of the first distillation column and comprises water and the homogenous catalyst mixture, and
   S7: introducing the first distillation mixture removed from the top of the first distillation column into the first condenser and condensing the first distillation mixture.

2. The process according to claim 1, wherein the reaction mixture, immediately prior to S3, has a temperature selected from a range from 100 to 210° C., and is at a pressure selected from a range from 15 to 100 bar (absolute), wherein the pressure is selected such that the reaction mixture in the reactor remains liquid at the selected temperature.

3. The process according to claim 1, wherein condensate from the first condenser is introduced into a first phase separator and is separated in the first phase separator into a first separation mixture and a second separation mixture, wherein the first separation mixture is in a form of an organic phase comprising methacrolein, and the second separation mixture is in a form of an aqueous phase.

4. The process according to claim 3, wherein the second separation mixture is introduced into a second distillation column and separated therein at least into a third distillation mixture and a fourth distillation mixture, wherein the third distillation mixture is in a form of a gas phase at the top of the second distillation column and comprises methacrolein, and the fourth distillation mixture is in a form of a liquid phase at the bottom of the second distillation column and comprises water.

5. The process according to claim 4, wherein the third distillation mixture is removed from the top of the second distillation column and introduced into the first condenser.

6. The process according to claim 4, wherein the third distillation mixture is introduced into and condensed in a second condenser, and condensate is removed from the second condenser and introduced into the first phase separator.

7. The process according to claim 4, wherein the third distillation mixture is introduced into and condensed in a second condenser, and condensate is removed from the second condenser and introduced into a second phase separator and is separated in the second phase separator into a third separation mixture and a fourth separation mixture, wherein the third separation mixture is in a form of an organic phase comprising methacrolein, and the fourth separation mixture is in a form of an aqueous phase.

8. The process according to claim 4, wherein the third distillation mixture is introduced into the first distillation column.

9. The process according to claim 4, wherein the third distillation mixture is introduced into the expansion vessel.

10. The process according to claim 1, wherein the second separation mixture is introduced into the first distillation column.

11. A preparation plant for preparation of methacrolein from formaldehyde and propionaldehyde in the presence of a homogeneous catalyst mixture based at least on an acid and a base,
wherein the preparation plant comprises:
- a reactor in which a reaction is performed under elevated pressure in a liquid phase, in which methacrolein is formed from formaldehyde and propionaldehyde in the presence of the homogeneous catalyst mixture based at least on the acid and the base,
- an expansion vessel wherein a first expansion mixture which is a fraction of a reaction mixture that goes into a gas phase as a result of an expansion of the reaction mixture, and a second expansion mixture which is a fraction of the reaction mixture remaining in a liquid phase after the expansion of the reaction mixture, are separated from one another, wherein the expansion vessel has a first outlet for removal of the first expansion mixture and a second outlet for removal of the second expansion mixture,
- a first distillation column which is fluidically connected to the second outlet of the expansion vessel and has a top and a bottom, wherein the first distillation column can separate the second expansion mixture at least into a first distillation mixture which is in a form of a gas phase and comprises methacrolein, and a second distillation mixture which is in a form of a liquid phase and comprises water and the homogenous catalyst mixture, and
- a first condenser which is fluidically connected to the first outlet of the expansion vessel and the top of the first distillation column, and wherein the first expansion mixture and the first distillation mixture are supplied and condensed.

12. The preparation plant according to claim 11, wherein the preparation plant has a first phase separator which is fluidically connected to the first condenser and wherein a first separation mixture of organic phase present in the condensate supplied by the first condenser is separated from a second separation mixture of aqueous phase present in the condensate supplied by the first condenser, wherein the first phase separator has a first outlet for removing the first separation mixture and a second outlet for removing the second separation mixture.

13. The preparation plant according to claim 12, wherein the preparation plant has a second distillation column which has a top and a bottom, and wherein the second separation mixture is separated at least into a methacrolein-containing third distillation mixture in a form of a gas phase and a water-containing fourth distillation mixture in a form of a liquid phase, and
wherein the preparation plant has a phase separator removal conduit arrangement which connects the second distillation column to the second outlet of the first phase separator, and which routes the second separation mixture from the second outlet of the first phase separator into the second distillation column.

14. The preparation plant according to claim 13, wherein a distillation column removal conduit arrangement fluidically connects the top of the second distillation column to the first condenser, and the third distillation mixture is routed through the distillation column removal conduit arrangement from the top of the second distillation column into the first condenser.

15. The preparation plant according to claim 13, wherein the preparation plant has a second condenser and a distillation column removal conduit arrangement that fluidically connects the top of the second distillation column to the second condenser, wherein the third distillation mixture is routed through the distillation column removal conduit arrangement from the top of the second distillation column into the second condenser and is condensed in the second condenser, and wherein the second condenser is fluidically connected to the first phase separator, by means of which condensate from the second condenser is routed from the second condenser further into the first phase separator.

16. The preparation plant according to claim 13, wherein the preparation plant further comprises:
- a second condenser,
- a distillation column removal conduit arrangement that fluidically connects the top of the second distillation column to the second condenser, wherein the third distillation mixture is routed through the distillation column removal conduit arrangement from the top of the second distillation column into the second condenser and is condensed in the second condenser, and
- a second phase separator fluidically connected to the second condenser, by means of which condensate from the second condenser is routed from the second condenser further into the second phase separator, wherein a third separation mixture of organic phase present in the condensate supplied by the second condenser is separated from a fourth separation mixture of aqueous phase present in the condensate supplied by the second condenser, wherein the second phase separator has a first outlet for removal of the third separation mixture and a second outlet for removal of the fourth separation mixture.

17. The preparation plant according to claim 13, wherein a distillation column removal conduit arrangement fluidically connects the top of the second distillation column to the first distillation column, and the third distillation mixture is routed through the distillation column removal conduit arrangement from the top of the second distillation column into the first distillation column.

18. The preparation plant according to claim 13, wherein a distillation column removal conduit arrangement fluidically connects the top of the second distillation column to the expansion vessel, and the third distillation mixture is routed through the distillation column removal conduit arrangement from the top of the second distillation column into the expansion vessel.

19. The preparation plant according to claim 13, wherein the preparation plant comprises a phase separator removal conduit arrangement that connects the first distillation column to the second outlet of the first phase separator, by means of which the second separation mixture is routed from the second outlet of the first phase separator into the first distillation column).

20. The process according to claim 2, wherein the reaction mixture, immediately prior to S3, has a temperature in a range from 130 to 180° C., and a pressure in a range from 22 to 50 bar (absolute).

* * * * *